United States Patent
Tomiyama et al.

(10) Patent No.: US 6,627,611 B2
(45) Date of Patent: Sep. 30, 2003

(54) C-GLYCOSIDES AND PREPARATION OF THEREOF AS ANTIDIABETIC AGENTS

(75) Inventors: Hiroshi Tomiyama, Hanishina-gun (JP); Yoshinori Kobayashi, Koushoku (JP); Atsushi Noda, Nagano (JP); Akira Tomiyama, Hanisina-gun (JP); Tsuyoshi Tomiyama, Hanishina-gun (JP)

(73) Assignee: Kotobuki Pharmaceutical Co Ltd, Nagano-ken (JP)

( * ) Notice: Subject to any disclaimer, the term of this patent is extended or adjusted under 35 U.S.C. 154(b) by 188 days.

(21) Appl. No.: 09/766,600

(22) Filed: Jan. 23, 2001

(65) Prior Publication Data
US 2001/0041674 A1 Nov. 15, 2001

(30) Foreign Application Priority Data
Feb. 2, 2000 (JP) ........................................ 2000-024970

(51) Int. Cl.$^7$ ............................ A61K 31/70; C07H 3/02
(52) U.S. Cl. ..................... 514/23; 536/1.11; 536/124
(58) Field of Search ................. 536/1.11, 124; 514/23

(56) References Cited

U.S. PATENT DOCUMENTS 6,414,126 B1 * 7/2002 Ellsworth et al. ........... 536/17.2

OTHER PUBLICATIONS

Link, J. T., et al "A method from preparing C–glycosides related to phlorizin" Tet. Lett., vol 41, pp. 9213–9217, 2000.*
Chemical Abstract No 90:138107 & R.A. Eade et al, Aust. J. Chem., (1978), 31(12), 2699–2706.
Chemical Abstract No 66:62641 & W.E. Hillis & T. Inoue, Phytochemistry, (1967), 6(1), 59–67.
Chemical Abstract No. 134:101086 & J.T. Link & B.K. Sorensen, Tetrahedron Lett., (2000), 41(48), 9213–9217.
Chemical Abstract No. 127:610 & M. Manickam et al, J. Nat. Prod. (1997), 60(6), 609–610.
Chemical Abstract No 99:172784 & E. Beltrami et al Phytochemistry, (1982), 21(12), 2931–2933.
Chemical Abstract No 97:146373 & H. Ohashi et al, Mokuzai Gakkaishi, (1982), 28(7), 463–472.
Chemical Abstract No 97:24104 & R. Tschesche & W. Widers, Leibigs Ann. Chem., (1982), 5, 902–907.

* cited by examiner

Primary Examiner—Kathleen K. Ponda
Assistant Examiner—Leigh C. Maier
(74) Attorney, Agent, or Firm—Sherman & Shalloway

(57) ABSTRACT

C-glycoside derivatives are disclosed, which are represented by the following formula (I) and its pharmaceutical acceptable salt, and which are useful for the treatment and/or prevention of diabetes and hypoglycemia.

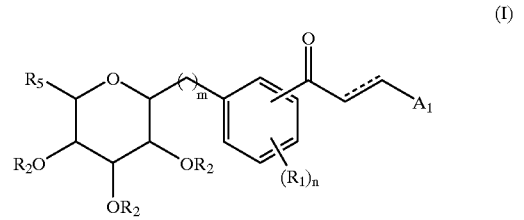

(I)

wherein: with the provisos that
$R_1$ is H, OH, lower alkyl, O-lower alkyl or

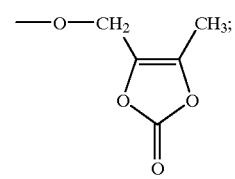

$R_2$ is H, —COO-lower alkyl,

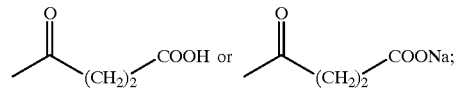

$R_5$ is —$CH_2OH$, —$CH_2OCO_2$-lower alkyl,

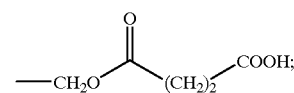

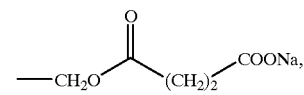

—$CH_2OSO_3H$, —COOH or —COONa;
wherein: A is

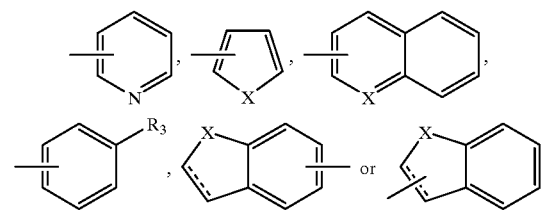

(with the provisos that X is oxygen atom, nitrogen atom or sulfur atom
$R_3$ is lower alkyl when m=0, and is lower alkyl, —OH or —O-lower alkyl when m=1, . . . means saturated or unsaturated carbon bond;
m is 0 or 1;
n is 0, 1 or 2;
above mentioned-lower alkyl means $C_1$–$C_5$.)
or a pharmaceutical acceptable salt.

3 Claims, No Drawings

C-GLYCOSIDES AND PREPARATION OF THEREOF AS ANTIDIABETIC AGENTS

BACKGROUND OF THE INVENTION

1. Field of the Invention

This invention regarding to new C-glycosides which are useful for the treatment and/or prevention of diabetes and a pharmaceutical composition containing these compounds as active ingredients. And this invention is also including the method of preparation of C-glycosides.

Current Technology

The anti-diabetic compounds which modulates energy valance and glucose levels in the body are required recently.

The $Na^+$-glucose cotransporter (SGLT) located on the chorionic membrane of the intestine and the kidney. Glucose is absorbed in the investive and the kidney mediated by SGLT.

The mechanism of inhibiting SGLT provides a novel approach to treat and/or prevent of diabetes. Because the inhibitory effect on SGLT may be excrete extra glucose into urine and as a result, prevent chronic hyperglycemia (Welch, C. A. et al., J.Natr., 1989,119(11)1698).

Phlorizin, O-glycosides, is reported as a specific inhibitor of SGLT. And the series of O-glycosides are synthesized and reported the anti-diabetics activity of these compounds (Hanga, M.et al., Chem.Pharm.Bull.1998,46(1)22, Tokukai 11-021243).

These series of O-glycosides, however, would be cleaved by glycosidase exsists in intestine when orally administrated.

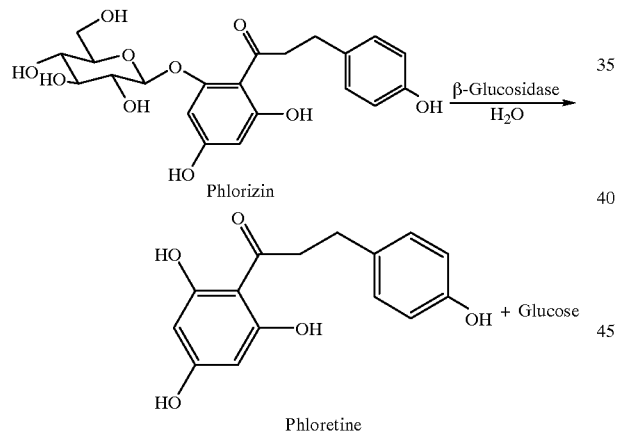

Phlorizin

Phloretine

And it is reported that phloretine, the aglycone of phlorizin, inhibit facilitated-type glucose transporter. For example, intravenously injection of to rats result the reduction of glucose levels in rat brain (Stroke,1983,14,388).

To overcome the stability against glycosidases, acids and bases, the chemistry of C-glycosides which replace of internal oxygen atom to carbone atom are reported (R. J. Linhardt.et al.,Tetrahedron, 1998, 54,9913., D. E. Levy,The Chemistry of C-Glycosides.Pergamon; Oxford,1995., M. H. D. Postema, C-Glycoside Synthesis.CRC Press;Boca Raton.1995). However, it is not reported that C-glycosides has strong SGLT inhibitor, so far.

The Subject of the Invention

The present invention concerns metabolic and hydrolytic stable C-glycosides compounds. These C-glycosides excrete extra glucose into urine and show hypoglycemic activity and a pharmaceutical composition containing these compounds as active ingredients. The present invention also includes the methods of preparing these C-glycosides compounds.

A Solution to the Invention

After elaborated to make C-glycosides which metabolic and hydrolytic stable for an anti-diabetics drug, the inventors found that new compounds as show general formula (I) had shown potent anti-diabetic activities and fulfilled this invention. Namely, the invention is the compounds as shown in general formula (I) and its pharmaceutically acceptable salts and a composition containing these compounds as active ingredients.

SUMMARY OF THE INVENTION

A novel C-glycosides and preparation of thereof as the treatment and/or prevention agent of diabetes and the blood glucose lowering agent are provided.

DETAILED DESCRIPTION OF THE INVENTION

It is that the compounds as shown in general formula (I) and its pharmaceutically acceptable salts.

Namely, the invention is the compounds as shown in general formula (I) and its pharmaceutically acceptable salts and a composition containing those compounds as active ingredients.

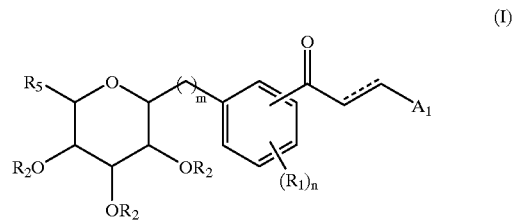

(I)

wherein: with the provisos that $R_1$ is H, OH, lower alkyl, O-lower alkyl or

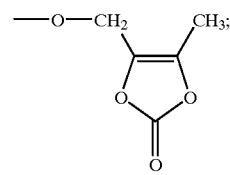

$R_2$ is H, —COO-lower alkyl,

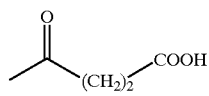

or

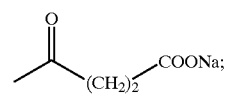

$R_5$ is —$CH_2OH$, —$CH_2OCO_2$-lower alkyl,

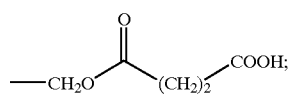

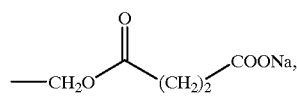

—$CH_2OSO_3H$, —COOH or —COONa;

wherein: A is

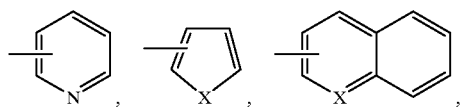

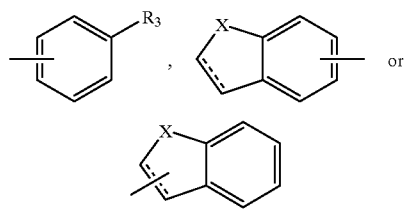

(with the provisos that X is oxygen atom, nitrogen atom or sulfur atom $R_3$ is lower alkyl when m=0, and is lower alkyl, —OH or —O-lower alkyl when m=1, . . . means saturated or unsaturated carbon bond;

m is 0 or 1;

n is 0, 1 or 2;

above mentioned-lower alkyl means $C_1$–$C_5$.)

Enforcement of Invention 48 compounds are exemplified as follow, but the invention is not limited to these compounds.

TABLE 1

| Compound | Structure | mp (° C.) | $[\alpha]D^{23}$/(c, solv.) |
|---|---|---|---|
| 1 | 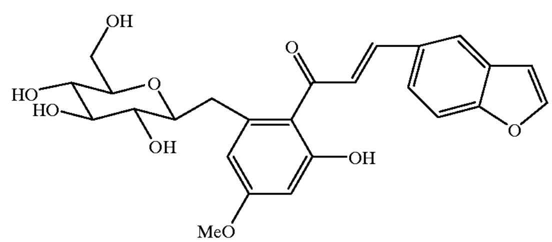 | 135–136 | −1.59(1, Py.) |
| 2 | 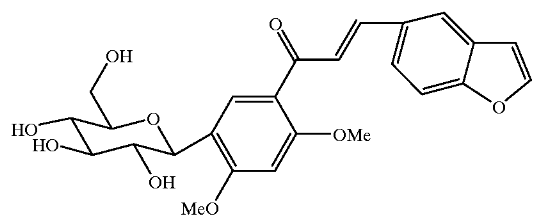 | 226–228 | −23.60(1, Py.) |
| 3 | 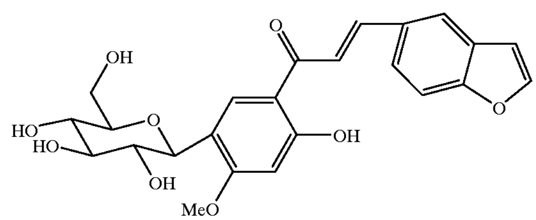 | >250 | −24.80(0.5, Py.) |
| 4 | 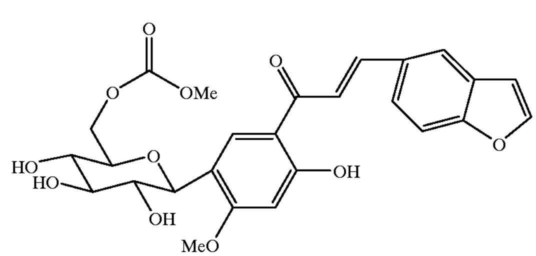 | 195–196 | −40.19(1, Py.) |

TABLE 1-continued

| Compound | Structure | mp (° C.) | $[\alpha]_D^{23}$/(c, solv.) |
|---|---|---|---|
| 5 | (structure) | 120–121 | −35.80(1, Py.) |
| 6 | (structure) | 120–121 | −10.80(1, Py.) |
| 7 | (structure) | 189–190 | −42.00(0.1, Py.) |

TABLE 2

| Compound | Structure | mp (° C.) | $[\alpha]_D^{23}$/(c, solv.) |
|---|---|---|---|
| 8 | (structure) | 228–229 | +57.19(1, Py.) |
| 9 | (structure) | 137–138 | −10.57 (0.643, CHCl$_3$) |
| 10 | (structure) | 181–183 | −66.13(0.5, Py.) |

TABLE 2-continued

| Compound | Structure | mp (° C.) | [α]D²³/(c, solv.) |
|---|---|---|---|
| 11 | 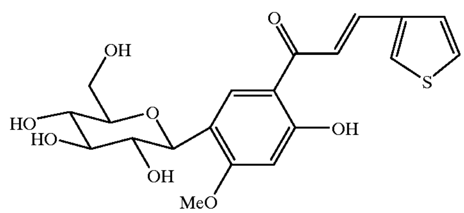 | 239–242 | −70.90(0.55, Py.) |
| 12 | 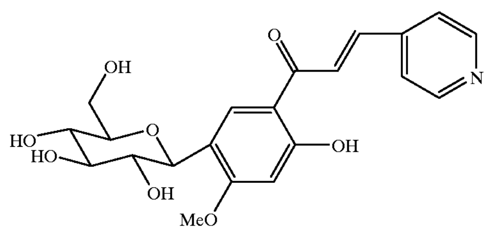 | 183–185 | −68.08(0.05, Py.) |
| 13 | 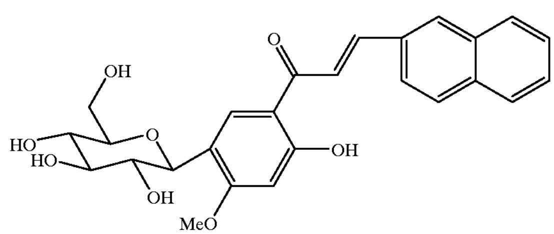 | 236–239 | −59.41(0.5, Py.) |
| 14 | 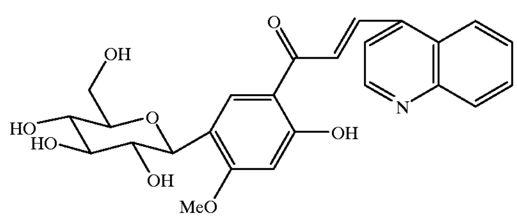 | 226–228 | −46(0.1, Py.) |

TABLE 3

| Compound | Structure | mp (° C.) | [α]D²³/(c, solv.) |
|---|---|---|---|
| 15 | 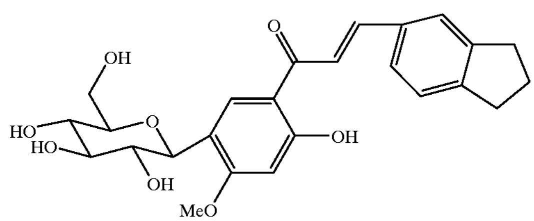 | 245–248 | −28.0(0.1, Py.) |
| 16 | 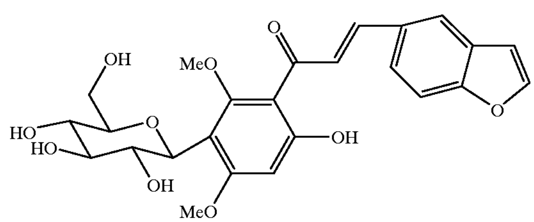 | 198–199 | +1.19(1, Py.) |

TABLE 3-continued

| Compound | Structure | mp (° C.) | $[\alpha]D^{23}$/(c, solv.) |
|---|---|---|---|
| 17 | 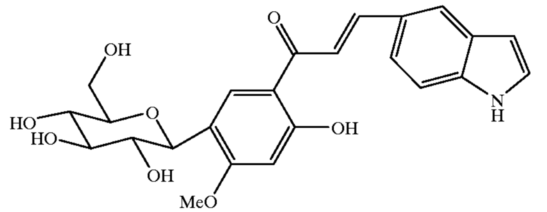 | 194–196 | −44(0.1, Py.) |
| 18 | 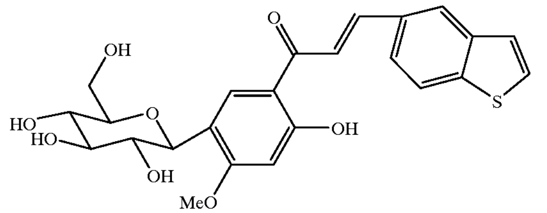 | 217–220 | −60(0.1, Py.) |
| 19 | 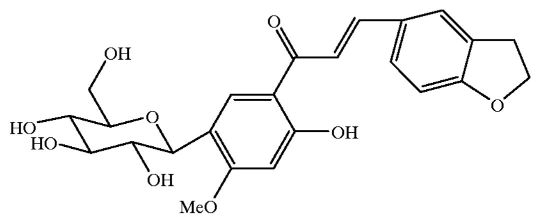 | 276–279 | −72(0.1, Py.) |
| 20 | 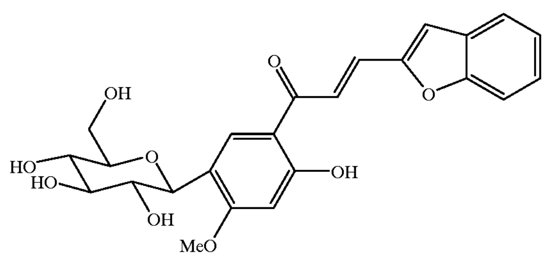 | 256–257 | −86.00(1, Py.) |
| 21 | 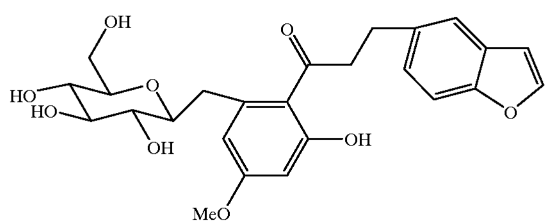 | 103–105 | −2.39(0.5, Py.) |

TABLE 4

| Compound | Structure | mp (° C.) | $[\alpha]D^{23}$/(c, solv.) |
|---|---|---|---|
| 22 | 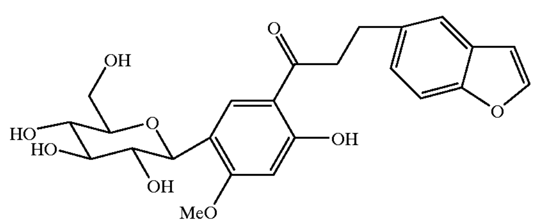 | 226–228 | −23.60(1, Py.) |

TABLE 4-continued

| Compound | Structure | mp (° C.) | $[\alpha]D^{23}$/(c, solv.) |
|---|---|---|---|
| 23 | 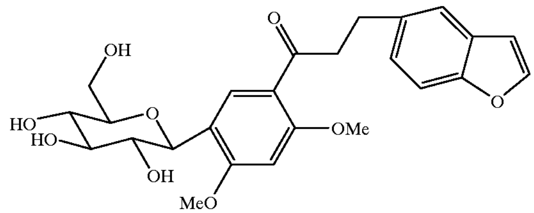 | 112–113 | −16.19(1, Py.) |
| 24 | 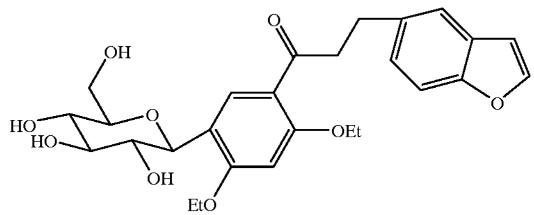 | 89–90 | −8.20(1, Py.) |
| 25 | 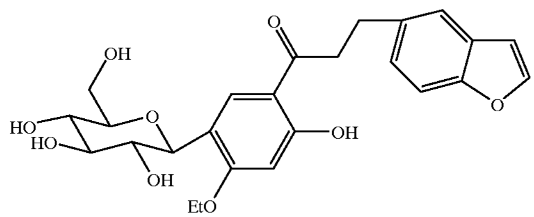 | 175–176 | −23.60(0.5, Py.) |
| 26 | 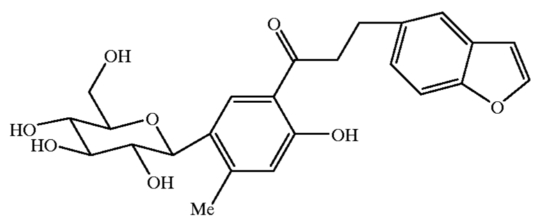 | 191–192 | +10.40(1, Py.) |
| 27 | 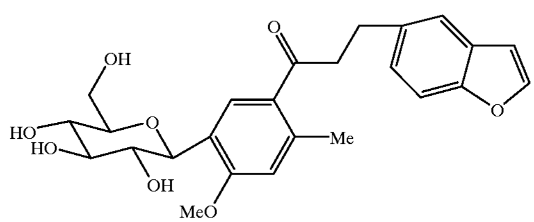 | 118–119 | −12.80 (0.5, $CH_2Cl_2$) |
| 28 | 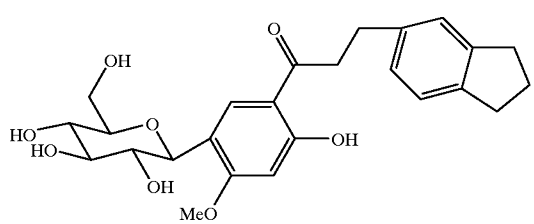 | 194–196 | −52.0(0.1, Py.) |

TABLE 5

| Compound | Structure | mp (° C.) | $[\alpha]_D^{23}$/(c, solv.) |
|---|---|---|---|
| 29 | 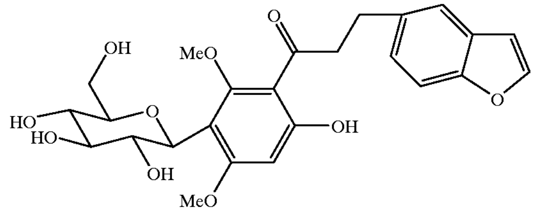 | 131–132 | −15.59(1.0, Py.) |
| 30 | 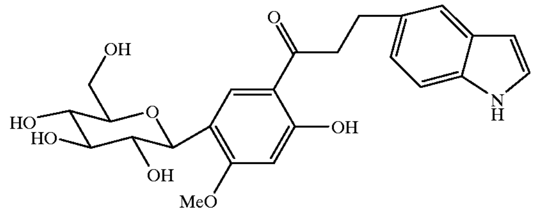 | 66–71 | −20(0.1, Py.) |
| 31 | 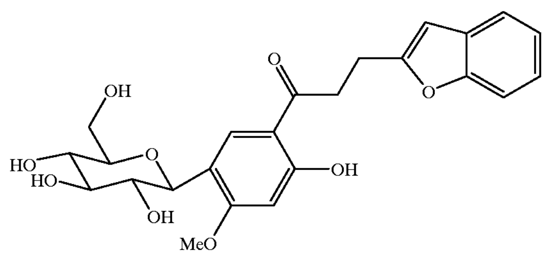 | 216–217 | −44.80(1, Py.) |
| 42 | 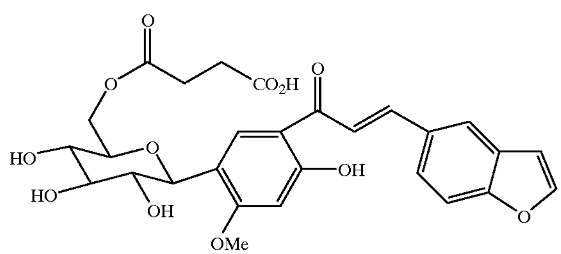 | 71–73 | |
| 43 | 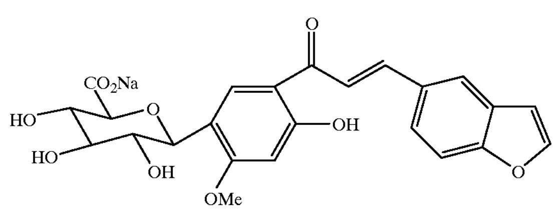 | 115–117 | |
| 44 | 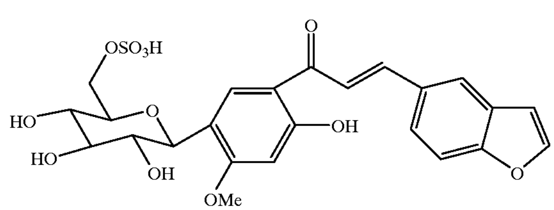 | 177–179 | |

TABLE 5-continued

| Compound | Structure | mp (° C.) | $[\alpha]D^{23}$/(c, solv.) |
|---|---|---|---|
| 45 | 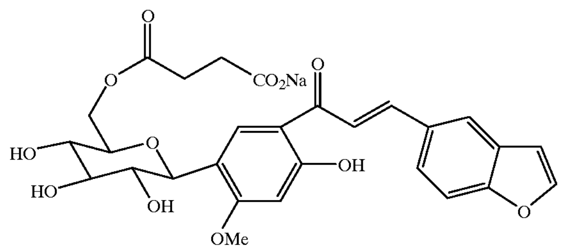 | 220> | |

TABLE 6

| Compound | Structure | mp (° C.) | $[\alpha]D^{23}$/(c, solv.) |
|---|---|---|---|
| 46 | 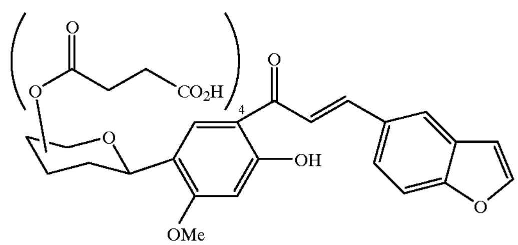 | 77–79 | |
| 47 | 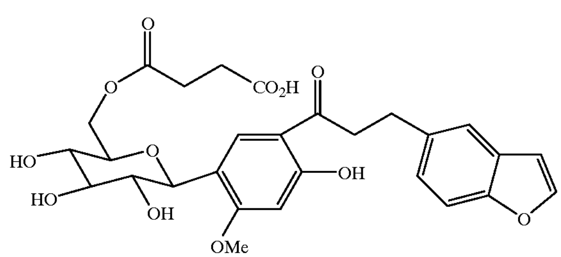 | 113–114 | −18.39 (0.5, MeOH) |
| 48 | 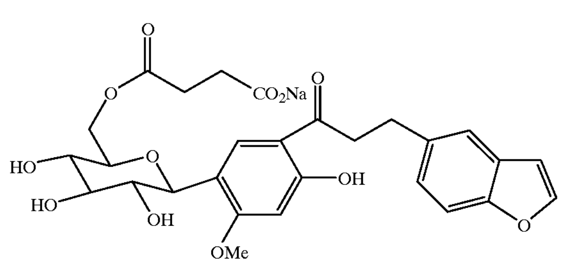 | 262 | −11.60 (0.5, MeOH) |

TABLE 6-continued

| Compound | Structure | mp (° C.) | [α]D²³/(c, solv.) |
|---|---|---|---|
| 49 | 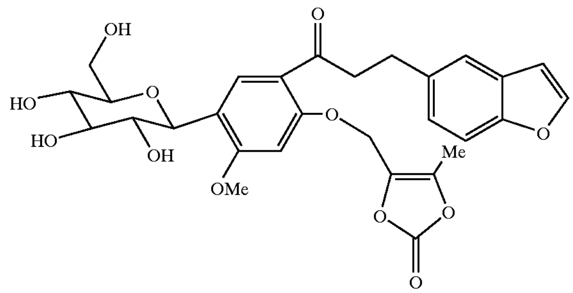 | 128–128.5 | +2.80 (1.0, MeOH) |
| 50 | 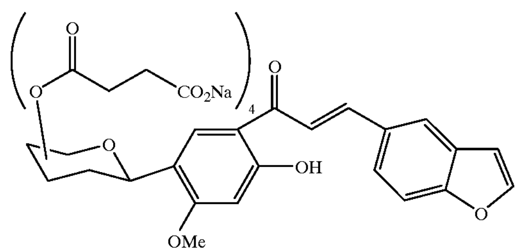 | >220 | |
| 51 | 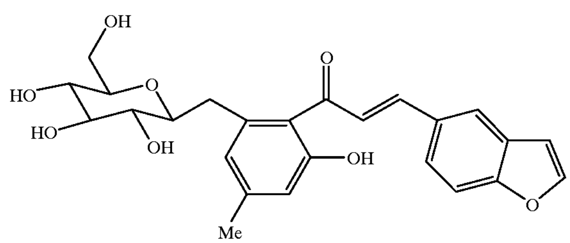 | 103–105 | +4.79 (1, CHCl₃) |
| 52 | 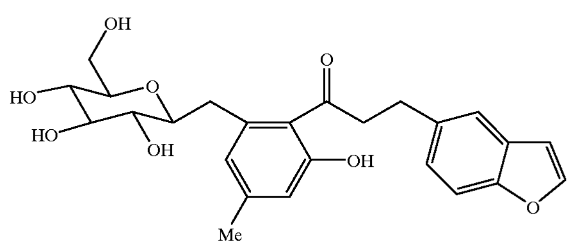 | 85–87 | −8.00 (1, CHCl₃) |

TABLE 7

| Compound | Structure | mp (° C.) | [α]D²³/(c, solv.) |
|---|---|---|---|
| 53 | 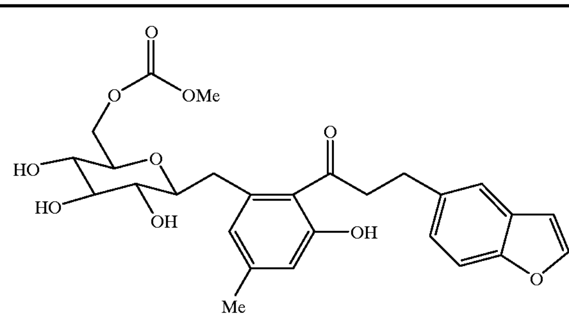 | 58–60 | −18.39 (1, CHCl₃) |

TABLE 7-continued
| Compound | Structure | mp (° C.) | $[\alpha]D^{23}$/(c, solv.) |
|---|---|---|---|
| 54 | 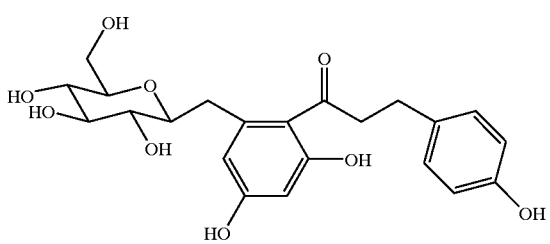 | 227–228 | −10.00 (1, CH$_3$OH) |
| 55 | 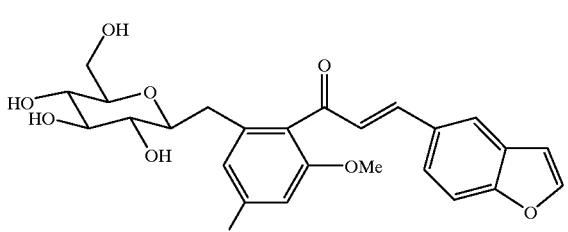 | 80–83 | +10.46 (1, CHCl$_3$) |
| 56 | 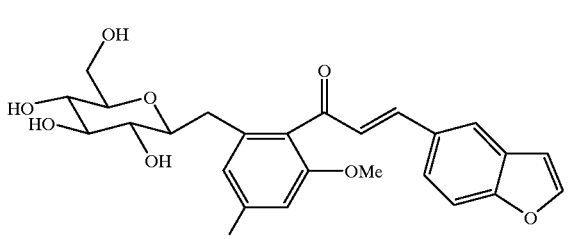 | amorphous | −1.19 (1, CHCl$_3$) |
| 57 | 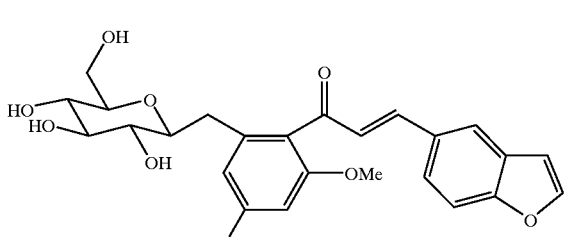 | 118–120 | −2.00 (1, CHCl$_3$) |
| 58 | 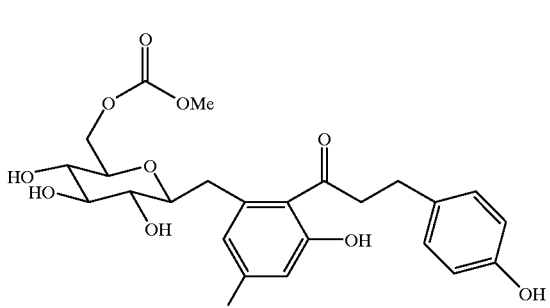 | 199–201 | −9.20 (1.0, MeOH) |
Typical preparations of the compounds of general formula (I) according to the invention are shown, but the invention is not limited to those examples.
The preparations of the compound of general formula (I).
(1) In case of R$_2$ is all hydrogen atoms.

The compounds can be obtained by means of the following diagram (wherein $R_1$, $R_4$, $A_1$, m, and n have the above-mentioned meaning): The compound of general formula (II) is converted to the compound of general formula (I) by the aldol reaction with aldehyde compound of general formula (IV), and followed by the catalytic hydrogenation of double bond of general formula I.

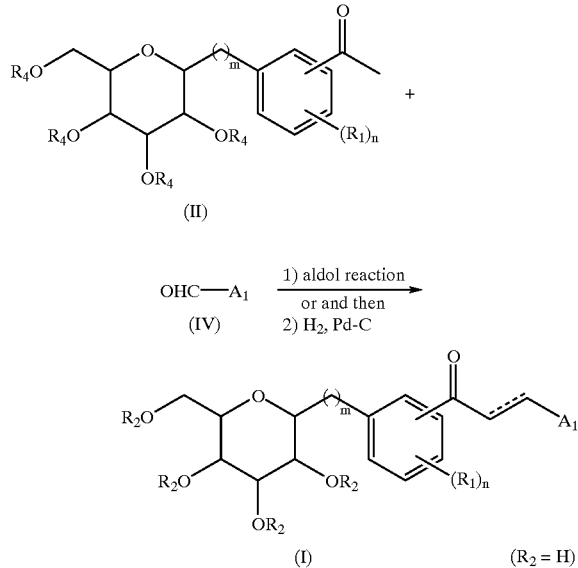

(2) In case of $R_1$ is —OH, $R_2$ is —H, or —COOCH$_3$.

The compounds can be obtained by means of the following reaction diagrams (wherein A, m, and n have the above-mentioned meaning): The phenolic hydroxy groups of the above-mentioned (I) is protected by allyl group, and then reacted with methyl chloroformate in the presence of base to obtain the compound of general formula (V). After removal of allyl groups of the compound (V) by the Pd catalyst, followed by the catalytic hydrogenation of double bond, if necessary, the compound of general formula (VI) is obtained.

(3) In case of $R_1$ is —OH, $R_2$ is —H or

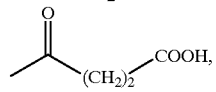

and $R_5$ is

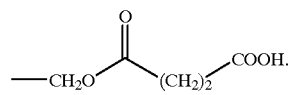

The compound can be obtained by means of the following reaction diagrams (wherein A and m have the above-mentioned meaning): The compound of general formula (I) is reacted with succinic anhydride in pyridine to obtain the compounds of general formula (XVII) and/or (XVIII).

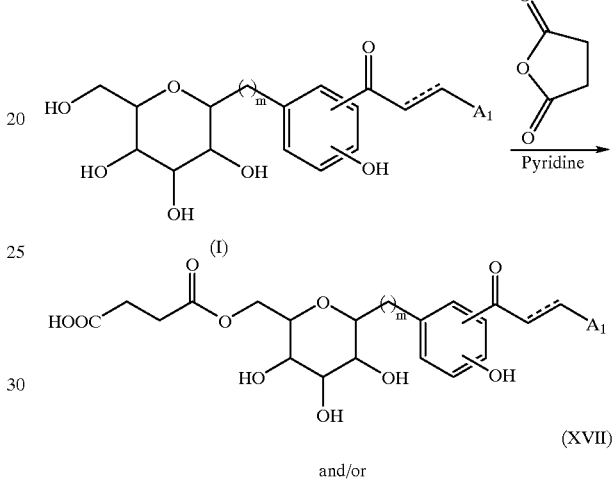

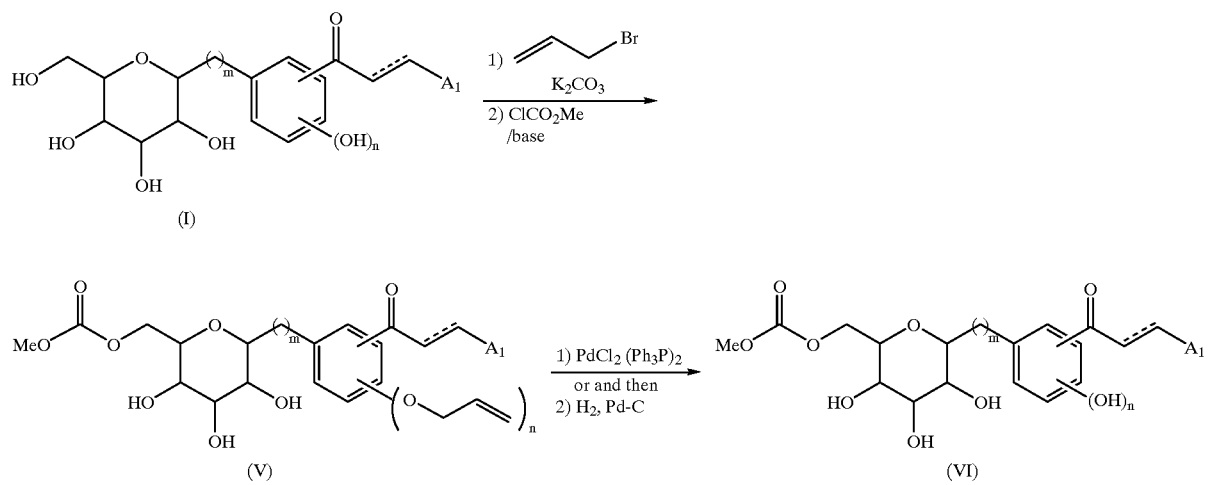

(4) In case of $R_2$ is all hydrogen atoms, $R_5$ is $CH_2OH$ and $R_1$ is

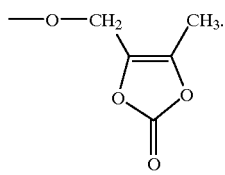

The compounds can be obtained by means of the following reaction diagram (wherein $A_1$ and m have the above-mentioned meaning): The phenolic hydroxy group of the compound of general formula (I) is reacted with 4-bromomethyl-5-methyl-1,3-dioxolene in the presence of base, to obtain the compound of general formula (XIX).

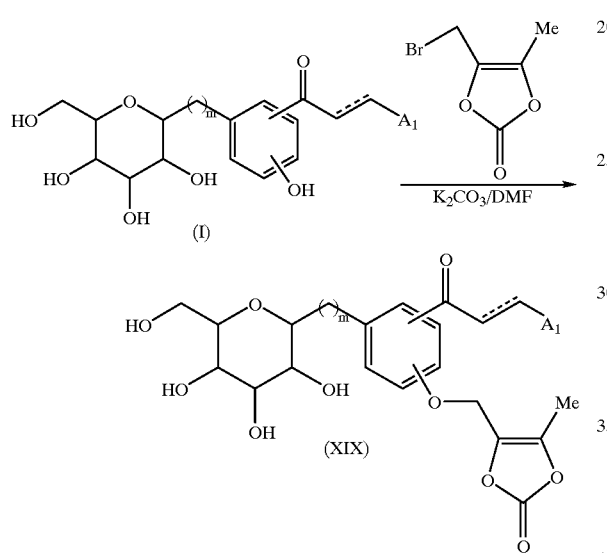

The preparations of the compound of general formula (II).

(a) In case of m=0

The compound can be obtained by means of the following reaction diagram (wherein $R_1$ and n have the above-mentioned meaning, X is halogen (Br, F, etc.), leaving group such as $CF_3.CO.O$—, and Bn is benzyl): The compound of general formula (VII) is reacted with benzene derivatives (VIII) in the presence of Lewis acid (e.g. $BF_3.Et_2O$, $SnCl_4$, $AlCl_3$, $AgOSO_2CF_3$ etc.) to synthesize the coupling compound (IX) (e.g. Jaramillo,C.et al.,Synthesis,1994,1)

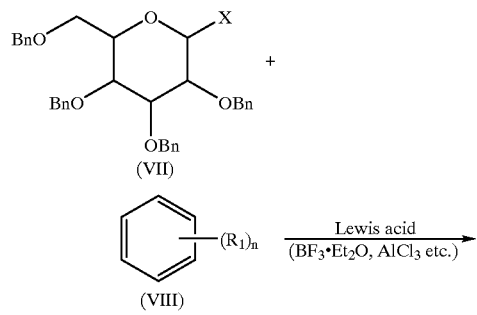

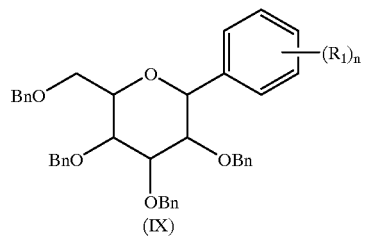

And the compound of general formula (IX) can be also obtained by using Grignards reaction of the compound (VII) with Grignards reagent (X) (e.g. Yokoyama,M.et al., Synthesis,1998,409).

The process is shown in the following reaction diagram.

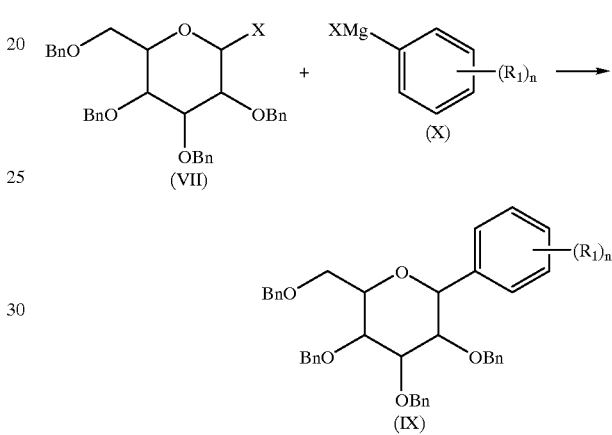

(b) In case of m=1

The compound can be obtained by means of the following reaction diagram (wherein $R_1$ and n have the above-mentioned meaning): The compound of general formula (XII) as a starting material is synthesized by the reaction of corresponding lactone (XI) with Tebbe reagent (Tebbe,F. N.,et al.,J.Am.Chem.Soc.,1978,100,3611). The compound of general formula (XII) is hydroborated with 9-borabicyclo[3,3,1]nonane (9-BBN) followed by Suzuki coupling reaction with the compound of general formula (XIII) in the presence of palladium catalyst, to obtain the compound of general formula (XIV) (e.g. Johnson,C. R.et al.,Synlett., 1997,1406).

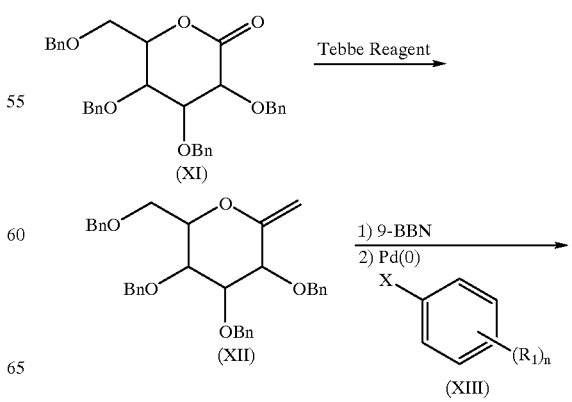

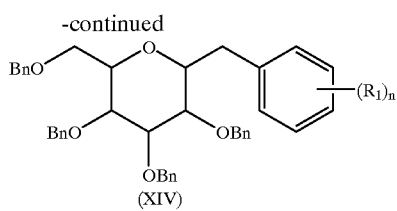

And the compound can be obtained by means of the following reaction diagram (wherein $R_1$, X, and n have the above-mentioned meaning): 2,3,4,6-Tetra-O-benzyl-1-thio-β-D-glucopyranose (XX) is reacted with arylmethylhalide (XXI) to convert sulfide (XXII). The oxidation of the compound (XXII) with OXONE® is led to sulfon (XXIII), and resulting compound (XXIII) is converted to olefin (XXIV) by Ramberg-Bäcklund rearrangement reaction. The compound of general formula (XIV) can be aslo synthesized in large scale by the hydrogenation of olefin (XXIV) in the present of palladium catalyst.

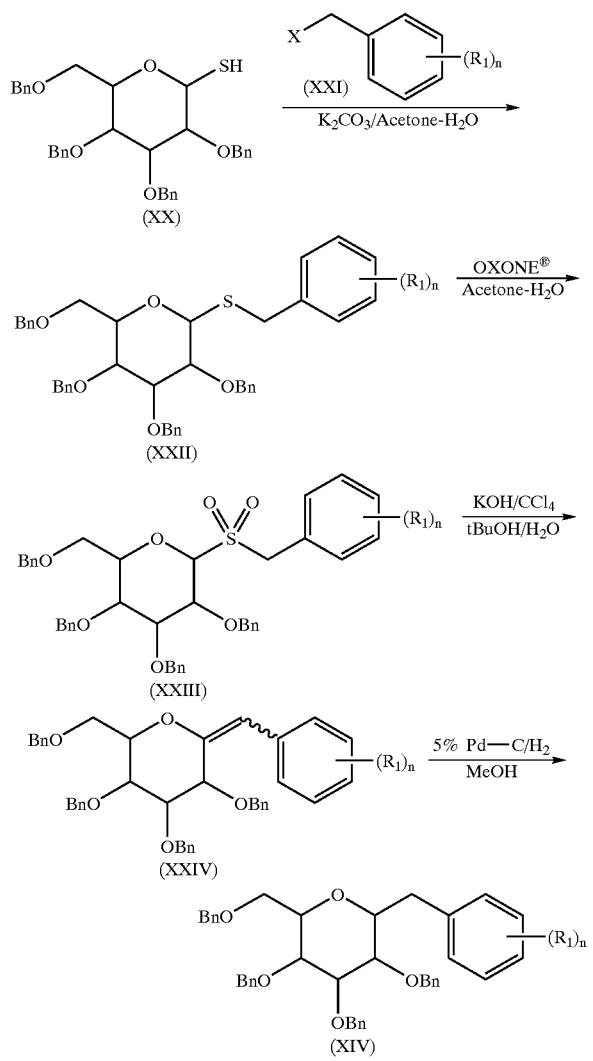

(c) The preparations of the compound of general formula (II)

The compounds can be obtained by means of the following reaction diagram (wherein $R_1$ and n have the above-mentioned meaning): The compounds of general formula (XV) obtained as described above process (a) or (b), is catalytically reducted to debenzylated derivatives, and after acetylation with $Ac_2O$ in pyridine, the compound of general formula (XVI) is afforded.

The compound of general formula (II) (in case of $R_4$ is acetyl group) is obtained by the Friedel-Crafts reaction of the compound of general formula (XVI). The compound of general formula (II) (in case of $R_4$ is hydrogen atom) can be also obtained by the subsequent deacetylation with NaOMe.

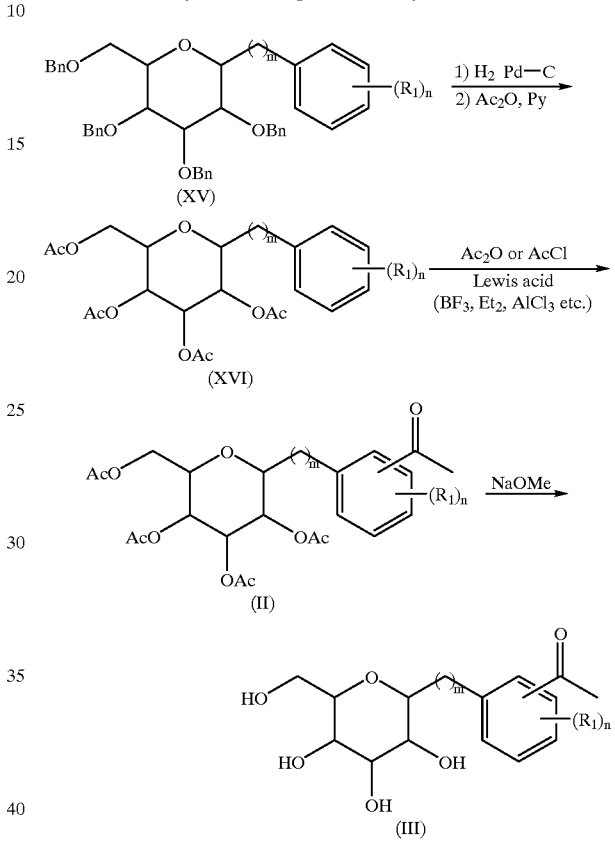

And in case of m=1, the compound of general formula (II) can be also obtained as shown in the following reaction diagram (wherein $R_1$, X and n have the above-mentioned meaning): When the Suzuki coupling reaction in above-mentioned process (b) is carried out, in stead of arylhalide (XIII), the derivatives attached acetyl group (XXV) is used to obtain the compound of general formula (XXVI).

Resulting compound can be converted to the compound of general formula (III) or (II) by the debenzylation or followed by acetylation.

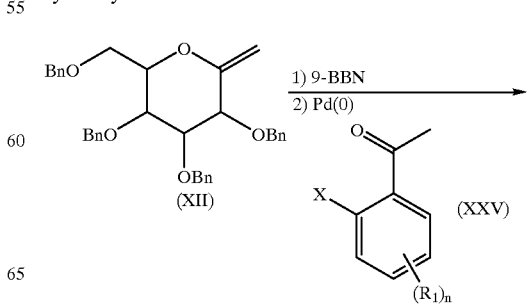

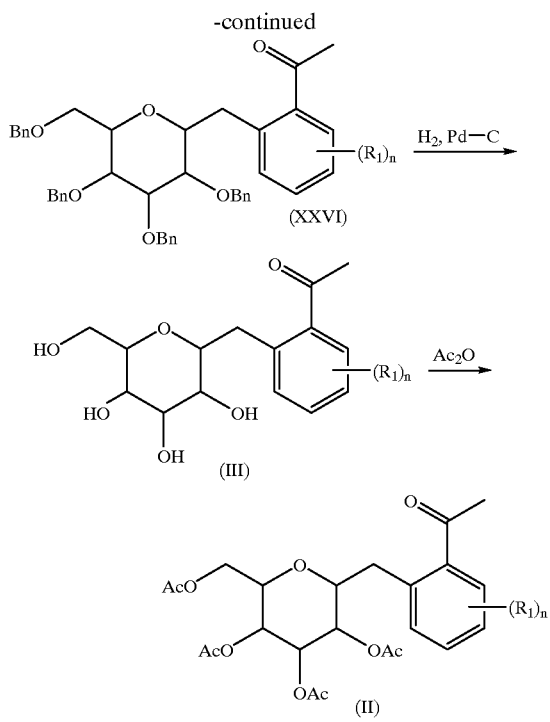

As pharmaceutical acceptable salts of a compound of general formula (I), sodium salt, potassium salt and inorganic base are mentioned.

In case of $A_1$ contains pyridine base, salts of inorganic and organic acids are mentioned. As the salt of inorganic acid, hydrochloride and sulfate are mentioned. As the salt of organic acid, acetate, succinate and fumalate are mentioned.

A compound of general formula (I) can be used itself or formulated to pharmaceutical product such as powder, granule, tablet and capsule by known pharmaceutical technology and can be orally administrable, It can be also administered not orally such as direct administration to rectal and in the form of injection. An effective dosage of the compound is from 10 to 1000 mg once to several times a day for adults, through it may be adjusted depending an age, a body weight and symptoms.

PHARMACOLOGICAL EXPERIMENT

The pharmacological test of urinary glucose excretion in rat is described that follow.

Measurement of Urinary Glucose Excretion in Rats 20 mg of test compounds were dissolved in 10 mL saline containing 20% dimethylsulufoxide.

Test compound (10 mg/5 mL/kg, i.p.) was administered twice an 8 hr interval to male SD rats (6 weeks old, 3 animals/group). An equal volume of vehicle was given to the control group. Urine was collected for 24 hr after first administration in metabolic cages.

The urine was centrifuged and urine volume was measured. Glucose concentration (mg/dl) was assayed using Glucose CII test Wako (Wako Pure Chemicals, Japan). The amounts of glucose excretion during 24 hr was calculated from the following equation.

Glucose secretion (mg/24 hr)=(A×B)/100

(A; the urine volume, B; the glucose concentration)
The result are shown in Table 8.

TABLE 8

| Compound | Dose (mg/kg) | Urinary glucose excretion (mg/24 hr) |
|---|---|---|
| 1 | 10 | 4.1 |
| 3 | 10 | 241 |
| 4 | 10 | 289 |
| 5 | 10 | 228 |
| 6 | 10 | 8.9 |
| 22 | 10 | 124 |

EXAMPLE

The following Example are provided only for the purpose of the preparation of the compound and not restrict the disclosed invention. The following compound 1–31 and 42–58 correspond to that of table 1–7.

Example 1

3-(Benzo[b]furan-5-yl)-1-(2'-β-D-glucopyranosylmethyl-6'-hydroxy-4'-methoxy)acrylophenone (Compound 1)

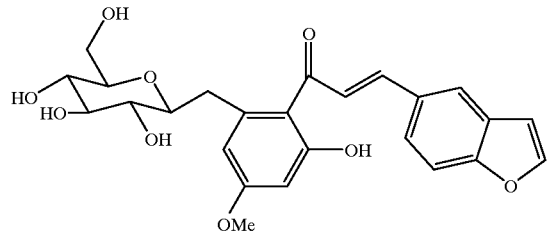

(a) 1-(3,5-Dimethoxyphenylmethyl)-1-deoxy-2,3,4,6-tetra-O-benzyl-β-D-glucopyranose (Compound 33)

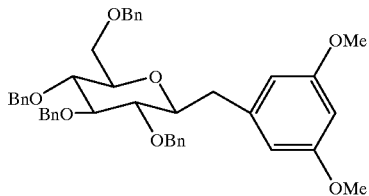

To 2,6-Anhydro-3,4,5,7-tetra-O-benzyl-1-deoxy-D-glucohept-1-enitol (2.0 g, XII), obtained from tetra benzyl-gluconolactone (XI) by Tebbe reaction, was added 9-BBN (0.5M in THF) at room temperature. After refluxing for 7 hr, the reaction mixture was cooled to room temperature and 3M $K_3PO_4$ (3.3 mL) was added. This was followed by the addition of 1,3-dimethoxyiodobenzene (1.2 g), and $PdCl_2$ (dppf) (160 mg). Resulting solution was stirred at room temperature for 3 hr. The reaction mixture was poured into $Et_2O$ (30 mL) and washed with brine. Organic layer was dried over $Na_2SO_4$. Filtration and obtained residue was followed by chromatography on silicagel (10:1 n-hexane/EtOAc) to give the compound 33 in 92% yield Mass (m/e): 675($M^+$+1),583,475,369,91(BP)
IR ($cm^{-1}$): 3022,2908,1455,1413,1389

$^1$H-NMR (CDCl$_3$): 2.75(dd,1H,J=14.0,9.0Hz),3.17(d,1H,J=9.0Hz),3.37(m, 2H), 3.52(m,1H),3.60~3.74(m,4H),3.70(S,6H),4.52~4.70(m,4H),4.82~4.96(m,4H),6.35(S,1H),6.42(S,2H),7.20~7.38(m,25H).

(i) 1-[(3,5-Dimethoxyphenyl)methylthio]-1-deoxy-2,3,4,6-tetra-O-benzyl-β-D-glucopyranose

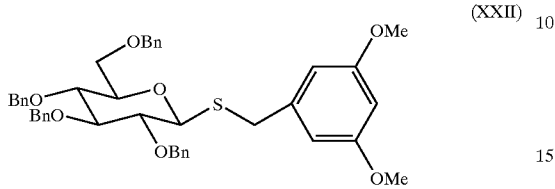

(XXII)

To a mixture of 2,3,4,6-tetra-O-benzyl-1-thio-β-D-glucopyranose (XX, 5.43 g) in acetone (40 mL), was added 3,5-dimethoxy benzylchloride (1.82 g) and a solution of K$_2$CO$_3$ (1.35 g) in H$_2$O (10 mL). The mixture was heated under reflux for 2 hr. After cooling, solvent was removed. The residue was dissolved in H$_2$O and extracted with AcOEt (2×30 mL). The organic layer was washed with Brine, dried over Na$_2$SO$_4$ and evaporated. The crude product was purified by silicagel column chromatography (8:1 n-hexane/AcOEt) to give the compound (XXII) in 90.5% yield.

IR (cm$^{-1}$): 3022,2854,1734,1596,1494,1455,1431,1398, 1350,1320,1293,1203, 1149, 1062,909,831,735,696

$^1$H-NMR (CDCl$_3$) δ: 3.71 (s,6H)3.39~3.98(m,8H),4.30(d,1H,J=9.8 Hz),4.53–4.89(m,8H),6.33(t,1H, J=2.0 Hz),6.51 (d,2H, J=2.5 Hz),7.15–7.37(m,20H).

(ii) 1-[(3,5-Dimethoxyphenyl) methyl]sulfonyl-1-deoxy-2,3,4,6-tetra-O-benzyl-β-D-glucopyranose

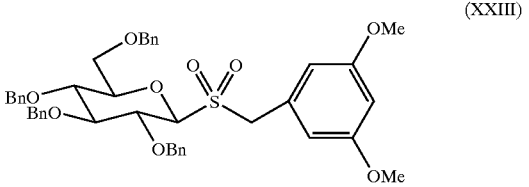

(XXIII)

To a mixture of 5.25 g of the compound obtained as described above (i) in acetone (45 mL), were added H$_2$O (15 mL) and OXONE® (13.7 g). The mixture was stirred at room temperature for 24 hr. Solvent was removed. The residue was dissolved in H$_2$O and extracted with AcOEt (2×50 mL). The organic layer was washed with brine, dried over Na$_2$SO$_4$, and evaporated. The crude product was purified by silicagel column chromatography (4:1 n-hexane/AcOEt) to give the compound (XXIII) in 79.5% yield.

IR(cm$^{-1}$): 3058,3022,2914,1731,1599,1494,1455,1431, 1401,1329,1269,1242, 1206,1152,1092,1026,996,933, 882,837,738,696,540

$^1$H-NMR (CDCl$_3$) δ: 3.51–4.09(m,6H),3.71 (s,6H),4.22(d, 1H,J=9.3 Hz),4.51–4.98(m,8H),4.57(s,2H),6.42(m,1H), 6.63(d,2H,J=2.4 Hz),7.15–7.34(m,20H)

(iii) 1-[(3,5-Dimethoxyphenyl)methylene]-1-deoxy-2,3,4,6-tetra-O-benzyl-β-D-glucopyranose

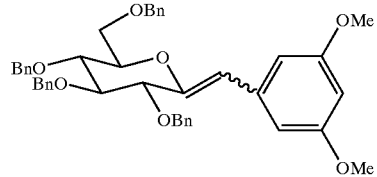

(XXIV)

To a mixture of 1.42 g of the compound obtained as described above (ii) in CCl$_4$ (15 mL) and 2-methyl-2-propanol (15 mL), were added H$_2$O (1.5 mL) and KOH (7 g). The mixture was heated under reflux for 1 hr. After cooling, the mixture was poured into ice-water, and extracted with AcOEt (2×20 mL). Organic layer was washed with H$_2$O (1×10 mL), brine (1×10 mL), dried over Na$_2$SO$_4$, and evaporated. The crude product was purified by silicagel column chromatography (4:1 n-hexane/AcOEt) to give the compound (XXIV) in 63.7% yield.

Mass (m/e): 672(M$^+$),247,181,135,91(BP),51

IR (cm$^{-1}$): 3058,3022,2920,2860,1656,1593,1494,1452, 1425,1359,1329,1299, 1257,1203,1149,1065,912,846, 735

$^1$H-NMR (CDCl$_3$) δ: 3.64(s,3H),3.73(s,3H),3.61–4.79(m, 14H),5.60–6.90(m, 4H),7.05–7.37(m,20H)

(iv) 1-(3,5-Dimethoxyphenylmethyl)-1-deoxy-2,3,4,6-tetra-O-benzyl-β-D-glucopyranose

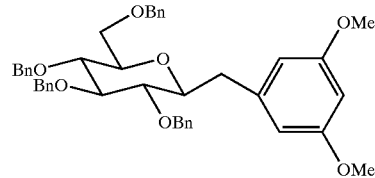

(XIV)

To a mixture of 0.76 g of the compound obtained as described above (iii) in MeOH (10 mL), was added 5% Pd-C (0.2 g). After stirring under hydrogen at room temperature for 30 min, the mixture was filtered and evaporated. The residue was purified by silicagel column chromatography (8:1 n-hexane/AcOEt) to give the compound (XIV) in 56.8% yield.

Mass (m/e): 675(M$^+$+1),583,475,369,91(BP)

IR (cm$^{-1}$): 3022,2908,1455,1413,1389

$^1$H-NMR (CDCl$_3$) δ: 2.65–3.11(dABq,2H,J=14.2 Hz), 3.32–3.74(m,7H),3.69(s, 6H),4.49–4.95(m,8H),6.30(t, 1H,J=2.0 Hz),6.46(d,2H,J=2.4 Hz),7.18–7.37(n, 20H)

(b) 1-(3,5-Dimethoxyphenyl)-1-deoxy-β-D-glucopyranose

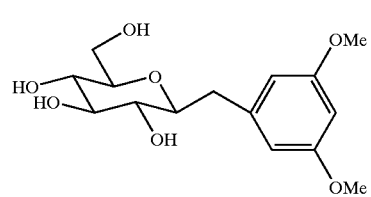

(Compound 34)

To a mixture of 3.0 g of the compound obtained as described above (a) in MeOH, was added 5% Pd-C (1.0 g). After stirring under hydrogen at room temperature for 15 min, the mixture was filtered off over a Celite® and evaporated to give the compound 34 in quantitative yield.

$^1$H-NMR (DMSO:CDCl$_3$=2:1): 2.57–3.28(m,7H),3.46–3.69 (dABq,2H),3.72(s, 6H),6.26(t,1H),6.47(d,2H)

(c) 1-(3,5-Dimethoxyphenylmethyl)-1-deoxy-(2,3,4,6-tetra-O-acetyl)-β-D-glucopyranose (Compound 35)

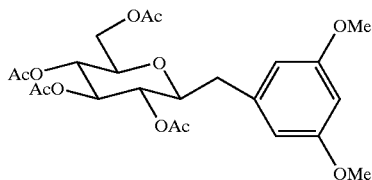

To a mixture of 1.0 g of the compound obtained as described above (b) in pyridine (10 mL) was added acetic anhydride (5 mL) at 0° C. The mixture was stirred at room temperature for 12 hr and poured into AcOEt (30 mL). The organic layer was washed with brine, dried over Na$_2$SO$_4$, and evaporated. The residue was purified by silicagel column chromatography (1:1 n-hexane/AcOEt) to give the compound 35 in 81% yield. mp=103–105° C.

Mass (m/e): 482(M$^+$),303,247,217,189,152(BP),109,81,51

IR (cm$^{-1}$): 1737, 1596, 1368, 1242

$^1$H-NMR (CDCl$_3$): 1.99,2.00,2.02,2.03(12H),2.74~2.76(m, 2H),3.78(S,6H), 3.58~5.19(m,7H),6.33~6.36(m,3H)

(d) 2-Hydroxy-4-methoxy-6-(2,3,4,6-tetra-O-acetyl-β-D-glucopyranosylmethyl)-acetophenone

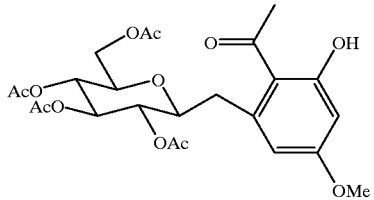

To a mixture of 1.2 g of the compound obtained as described above (c) in diethylether (20 mL), was dropwised a solution of AlCl$_3$ (3.5 g) in Et$_2$O (20 mL) at 0° C. After stirring at room temperature for 12 hr, the mixture was poured into diluted hydrochloric acid, and extracted with methylene chloride. Organic layer was washed with satd. NaHCO$_3$ aq. and brine, dried over Na$_2$SO$_4$, and evaporated. The crude product was purified by silicagel column chromatography (4:1 n-hexane/AcOEt) to give the compound 36 in 58% yield (742 mg). mp=159–160° C.

Mass (m/e): 510(M$^+$),474,417,373,331,275,233,205,169, 139,109(BP),81,47

IR (cm$^{-1}$): 3400,2914,1752,1686,1605,1371,1218,1173

$^1$H-NMR (CDCl$_3$): 2.00~2.03(m,12H),2.65(S,3H), 3.61~3.68(m,2H),3.90(S, 3H),4.06~5.21(m,7H),6.23(S, 1H),6.44(S,1H),13.27(S,1H)

(e) 3-(Benzo[b,]furan-5-yl)-1-(2'-β-D-glucopyranosylmethyl-6'-hydroxy-4'-methoxy) acrylophenone (Compound 1)

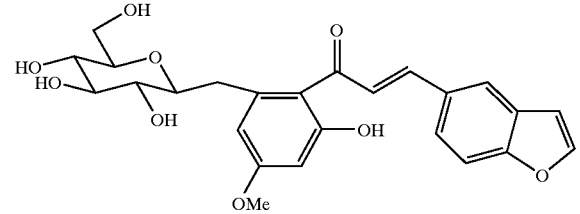

To a mixture of 203 mg of the compound obtained as discribed above (d) and 5-benzofuranaldehyde (70 mg) in EtOH (2 mL), was added 0.4 mL of 50% KOH at 0° C. After stirring at room temperature for 12 hr, the mixture was adjusted to ca pH 4 with 10% HCl, and extracted with ethyl acetate. The organic layer was washed with satd. NaHCO$_3$ and brine, dried over Na$_2$SO$_4$, and evaporated. The crude product was purified by silicagel column chromatography (9:1 chloroform/MeOH) to give the compound 1 (102 mg) in 55% yield. mp=135–136° C. [α]$^{23}$D=−1.59 (C=1, Py.)

Mass (m/e): 470(M$^+$),434,403,350,319,290,261,219,191, 164,131(BP),91,60

IR (cm$^{-1}$): 3370,2914,1605,1440,1263,1197,1155,1086, 1026

$^1$H-NMR (CDCl$_3$): 2.63~2.65,2.95~3.00(m,3H),3.07~3.78 (m,6H),3.81(S, 3H) 6.40,6.48(ABq,2H,J=2.4 Hz),6.79(S, 1H),7.13~7.73(ABq,2H,J=15.6 Hz), 7.49~7.57(ABq,2H, J=8.3 Hz),7.65(S,1H),7.81(S,1H),10.02(brs,1H)

Example 2

3-(Benzo[b]furan-5-yl)-2'-β-D-glucopyranosylmethyl-6'-hydroxy-4'-methoxypropiophenone (Compound 21)

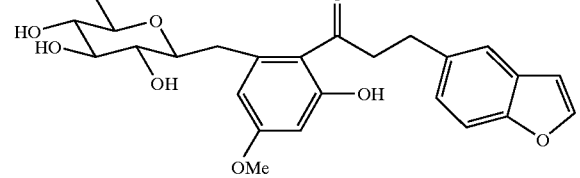

To a mixture of 0.13 g of the compound obtained as described above (e) of Example 1 in 1:1 THF-MeOH (10 mL), was added 0.1 g of 5% Pd-C. After stirring under hydrogen at room temperature for 30 min, the mixture was filtered off over a Celite® and evaporated. The crude product was purified by silicagel column chromatography (10:1 chloroform/MeOH) to give the compound 21 (80 mg) in 61% yield. mp=103–105° C. [α]$^{23}$$_D$=−2.39 (C=0.5, Py.)

Mass (m/e): 472(M$^+$),434,374,319,291,243,205,177,131 (BP),91,57

IR (cm$^{-1}$): 3400,2914,1605,1443,1266,1197,1104

$^1$H-NMR (CDCl$_3$,DMSO=1:2): 3.04~3.13(m,2H),3.83(S, 3H),3.34~5.60(m, 11H),6.42~7.83(m,7H)

Reference 1

2-(β-D-glucopyranosylmethyl)-6-hydroxy-4-methoxy-acetophenone (Compound 32)

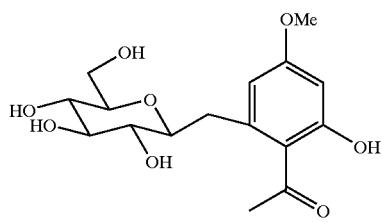

To a mixture of 336 mg of the compound 36 obtained as described above (d) of Example 1 in methanol (5 mL), was added 28 mg of Sodium methoxide at 0° C. After stirring at room temperature for 1 hr. Ion exchange resin (ca 1 g) was added and stirred for 10 min, filtered, and evaporated. The residue was purified by silicagel column chromatography (10:1 chloroform/MeOH) to give the compound 32 (225 mg) in 99% yield. The compound 32 was also used as a material, when the compound 1 and 2 were synthesized. mp=98–99° C. $[\alpha]^{23}_D$=−2.80 (C=1.0, Py.)
Mass (m/e): 342($M^+$),324,306,221,191(BP),165,137,115, 91,69,51
IR ($cm^{-1}$): 3388,1608,1356,1263,1200,1155,1080
$^1$H-NMR (CDCl$_3$.DMSO=1:2): 2.46(S,3H),2.55~2.61(m, 1H),2.91(t,1H, J=9.3,8.8 Hz),2.98~3.19(m,5H),3.42~3.65 (dABq,2H,J=11 Hz),3.72(S,3H), 4.14(brs,1H),4.79,4.83 (brs,2H),4.95(brs,1H),6.27(d,1H,J=2.0 Hz),6.41(d, 1H,J= 2.4 Hz),9.86(S,1H)

Reference 2

2,4-Dimethoxy-5-(2,3,4,6-tetra-O-acetyl-β-D-glucopyranosyl)acetophenone (Compound 37)

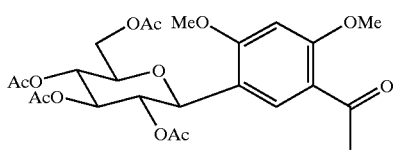

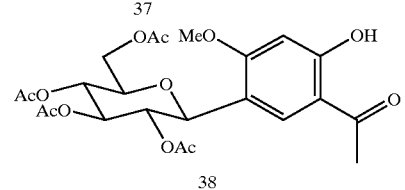

Friedel-Crafts reaction of 2,3,4,6-tetra-O-acetyl-1-(2,4-dimethoxyphenyl)-1-deoxy-β-D-glucopyranose (17.8 g), obtained by widely known method (R.Tschescheetal,et al., Liebigs Ann.Chem.902~907,1982), with aluminum chloride and acetic anhydride gave the reported compound 38 in 57% yield (10.78 g). And the compound 37 was also obtained in 10.1% yield (1.95 g) as a by-product. The compound 37 and 38 were used as a material to synthesize the compound 23 and 3, respectively. The measured value was shown below.
Mass (m/e): 510($M^+$),317,275(BP),209,179,139,97,69

IR ($cm^{-1}$): 3460,2939,1746,1653,1605,1578,1500,1443, 1368
$^1$H-NMR (CDCl$_3$): 1.77(S,3H),2.01(S,3H),2.05(S,3H),2.08 (S,3H),2.56(S,3H), 3.78~3.81(m,1 H),3.92(S,3H),3.93(S, 3H),4.12~4.26(dABq,2H,J=12.2 Hz), 4.71(d,1H,J=10.3 Hz),5.21(t,1H,J=9.6 Hz),5.32(t,1H,J=9.6 Hz),5.44 (t,1H, J=10.3 Hz),6.39(S,1H),7.88(S,1H)

Example 3

3-(Benzo[b]furan-5-yl)-3'-β-D-glucopyranosyl-6'-hydroxy-4'-methoxyacrylophenone (Compound 3)

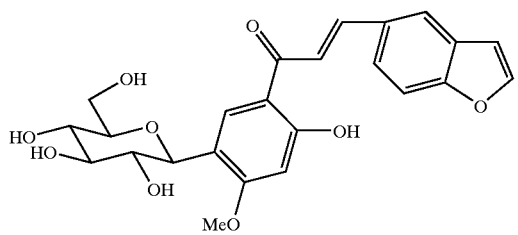

To a mixture of 2.0 g of the compound 38 obtained by widely kown method (R.Tschesche,et al.,Liebigs Ann.Chem.902~907,1982) and 0.71 g of 5-benzofuranaldehyde in ethanol (25 mL), was added 50% KOH at 0° C. The mixture was stirred at room tempareture for 12 hr. Then, to the mixture was added water, and washed with chloroform. Aqueous layer was adjusted to pH 3 with 10% hydrochloric acid, and extracted with chloroform. This chloroform layer was washed with brine, dried over Na$_2$SO$_4$, and evaporated. The residue was purified by silicagel column chromatography (10:1 chloroform/MeOH) to give the compound 3 (1.15 g) in 63% yield. mp>250° C. $[\alpha]^{23}_D$=−24.80 (C=0.5, Py.)
Mass (m/e): 456($M^+$),259,195,145,177,66(BP)
IR($cm^{-1}$): 3376,2908,1632,1566,1497,1446,1368,1281, 1260
$^1$H-NMR (CDCl$_3$.DMSO=1:2): 3.22~3.57(m,4H),3.73(d, 2H),3.88(s,3H),4.48(d, 1H),6.51(s,1H),6.98(d,1H),7.64 (d,1H),7.87~8.09(m,3H),8.15(s,1H), 8.16(d,1H),13.61(s, 1H)

Example 4

3-(Benzo[b]furan-5-yl)-3'-β-D-glucopyranosyl-4'-methoxy-6'-(2-propen-1-yl)oxy-acrylophenone (Compound 39)

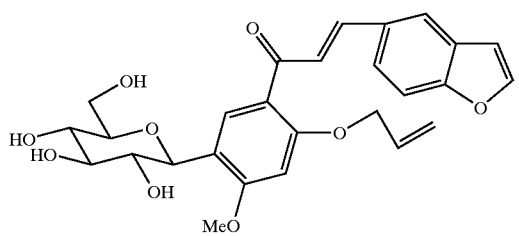

To a solution of the compound 3 (1.15 g) in acetone (20 mL) were added potassium carbonate (0.97 g) and allylbromide (0.3 mL), the reaction mixture was heated under reflux for 12 hr. The reaction mixture was poured into ice-water, and extracted with chloroform. Organic layer was washed with brine, dried over Na$_2$SO$_4$, and concentrated. The crude product was purified by silicagel column chromatography (20:1 chloroform/MeOH) to give the compound 39 (1.04 g) in 83% yield. mp=139–140° C. $[\alpha]^{23}_D$=−14.60 (C=1, Py.)

Mass (m/e): 497(M$^+$+1),435,358,311,283,253,207,177(BP), 147,119,92,65
IR (cm$^{-1}$): 3400,2896,1608,1575,1443,1314,1260,1200, 1122,1083
$^1$H-NMR (CDCl$_3$:CD$_3$OD=9:1): 3.45~3.47(m,1H), 3.54~3.65(m,3H),3.73~3.89 (dABq,2H,J=12.2 Hz),3.93 (S,3H),4.68~4.72(m,3H),5.31(dd,1H,J=10.3, 10.7 Hz), 5.48(dd,1H,J=17.1,17.6 Hz),6.06~6.13(m,1H),6.54(S, 1H),6.82(S, 1H),7.52(d,1H,J=8.4 Hz),7.59(d,1H,J=8.0 Hz),7.64(S,1H),7.69(S,1H),7.80~7.84(S+m,3H)

Example 5

3-(Benzo[b]furan-5-yl)-3'-(6-O-methoxycarbonyl-β-D-glucopyranosyl)-4'-methoxy-6'-(2-propen-1-yl)oxy-acrylophenone (Compound 40)

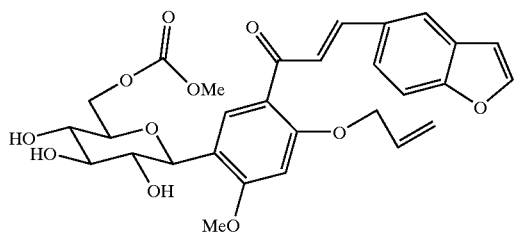

To a solution of compound 39 (0.97 g) and 2,4,6-collidine (2.6 mL) in methylene chloride (5 mL) was dropwised a solution of methyl chloroformate (0.18 mL) in methylene chloride, the reaction mixture was stirred at room temperature for 2 hr. The reaction mixture was poured into diluted hydrochloric acid, and extracted with ethyl acetate. Organic layer was washed with satd. NaHCO$_3$ and brine, dried over Na$_2$SO$_4$, and concentrated. The crude product was purified by silicagel column chromatography (20:1 chloroform/MeOH) to give the compound 40 (0.77 g) in 71% yield. mp=137–138° C. $[\alpha]^{23}_D$=−4.79 (C=1, Py.)

Mass (m/e): 554(M$^+$),505,478,446,404,361,310,282,243, 213(BP),183,156,124
IR (cm$^{-1}$): 3400,2908,1743,1608,1575,1503,1443,1263, 1197,1125
$^1$H-NMR (CDCl$_3$): 3.07(d,1H,J=3.6 Hz),3.46,3.50(brs,2H), 3.63~3.85(m,4H), 3.76(S,3H),3.90(S,3H),4.43~4.47 (ABq,2H),4.65~4.66(m,2H),4.71(d,1H, J=9.8 Hz),5.28 (dd,1H,J=10.7,10.2 Hz),5.45(dd,1H,J=17.1 Hz), 6.02~6.09(m, 1H),6.48(S,1H),6.75,7.65(d,2H,J=2.4 Hz), 7.48~7.58(ABq,2H,J=8.4 Hz), 7.57(S,1H),7.76,7.81(d, 2H,J=1.2 Hz), 7.85(S,1H)

Example 6

3-(Benzo[b]furan-5-yl)-3'-(6-O-methoxycarbonyl-β-D-glucopyranosyl)-6'-hydroxy-4'-methoxy-acrylophenone (Compound 4)

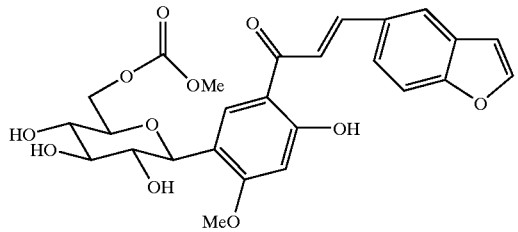

To a solution of the compound 40 (0.35 g) in acetonitrile (3 mL) was added PdCl$_2$ (Ph$_3$P)$_2$ (14 mg) and ammonium formate (0.24 g), the reaction mixture was heated under reflux for 12 hr, filtered, and concentrated. The crude product was purified by silicagel column chromatography (40:1 chloroform/MeOH) to give the compound 4 (0.13 g) in 39.3% yield. mp=195–196° C. $[\alpha]^{23}_D$=−40.19 (C=1, Py.)
Mass (m/e): 514(M$^+$),438,378,336,307,257,219,163(BP), 131,74
IR (cm$^{-1}$): 3400,2902,1746,1629,1560,1440,1371,1260
$^1$H-NMR (DMSO:CDCl$_3$=2:1): 3.37~3.39(m,1H), 3.47~3.51(m,1H),3.65(S,3H), 3.75~3.79(ABq,1H),3.88 (S,3H),4.12~4.17(m,1H),4.40~4.47(m,2H), 4.83(d,1H,J= 5.4 Hz),5.07(d,2H,J=3.4 Hz),5.19(d,2H,J=4.4 Hz),6.53(S, 1H), 6.99(S,2H),8.07(S,2H),7.65(d,2H,J=8.3 Hz),7.90(d, 2H,J=8.8 Hz),7.97(S, 1H),8.18(S,1H),13.61(S,1H)

Example 7

3-(Benzo[b] furan-5-yl)-3'-(6-O-methoxycarbonyl-β-D-glucopyranosyl)-6'-hydroxy-4'-methoxy-propiopenone (Compound 5)

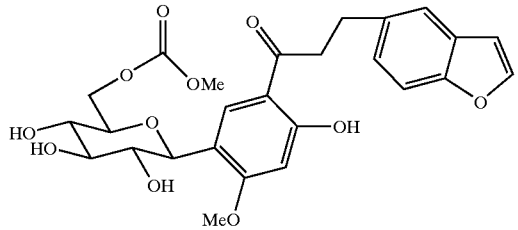

To a solution of the compound 4 (114 mg) in MeOH-THF (1:1, 2 mL) was added 5% Pd-C (50 mg), the reaction mixture was stirred under hydrogen at room temperature for 15 min. The reaction mixture was filtered and concentrated. The crude product was purified by silicagel column chromatography (40:1 chloroform/MeOH) to give the compound 5 (88 mg) in 77% yield. mp=120–121° C. $[\alpha]^{23}_D$=−35.80 (C=1, Py.)
Mass (m/e): 516(M$^+$),403,348,307,277,227,193,163,120,91, 62(BP)
IR (cm$^{-1}$): 3394,2908,1743,1629,1494,1443,1337,175,1206
$^1$H-NMR (CDCl$_3$): 2.12(d,1H,J=3.9 Hz),2.88(d,1H,J=2.0 Hz),2.96~3.00(m, 2H),3.15~3.24(m,3H),3.48~3.68(m, 4H),3.75(S,3H),3.87(S,3H),4.40~4.51(dABq,2H), 4.53~4.62(m,2H),4.63(d,1H),6.44(S,1H),6.72(d,1H, J=7.8 Hz),6.99(d,1H,J=6.8 Hz),7.09(S,1H),7.68(S,1H), 12.86(S,1H)

Reference 3

1-(4-methoxy-2-methylphenyl)-1-deoxy-(2,3,4,6-tetra-O-benzyl-β-D-glucopyranose (Compound 41)

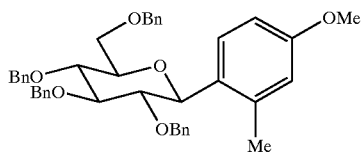

To a solution of 2,3,4,6-tetra-O-benzyl-D-glucopyranosyl fluoride (13.6 g) in THF (50 mL) was dropwised a solution of 4-methoxy-2-methylphenyl magnesium bromide in THF (prepared from magnesium (6 g) and 2-bromo-5-methoxytoluene (50 g)) at 0° C. The reaction mixture was stirred at room temperature for 12 hr, and poured into ice-water, then neutralized with 10% hydrochloric acid, and extracted with ethyl acetate. Organic layer was washed with satd. $NaHCO_3$ and brine, dried over $Na_2SO_4$, and concentrated. The residue was purified by silicagel column chromatography (8:1 n-hexane/ethyl acetate) to give the compound 41 (13.1 g) in 81% yield. The compound 41 was used as a material to synthesize the compound 9 and 27.

Mass (m/e): 644($M^+$),553,433,341,293,241,181(BP)135,92, 50
IR ($cm^{-1}$) (Neat): 3052,3016,2890,2854,1608,1578,1497, 1452,1393 cm–1
$^1$H-NMR ($CDCl_3$): 2.37(s,3H),3.52~3.85(m,6H),3.81(s, 3H),4.36(d,1H),4.46~4.96(m,8H),6.71(s,1H),6.78(d,1H) 6.92~7.33(m,20H),7.39(d,1H)

Example 8–23

According to a similar procedure described in Example 3, the compound 2, 6–20 were synthesized via aldol reaction, using acetophenone derivatives as a starting materials.

Example 24–34

According to a similar procedure described in Example 2, the compound 21–31 were synthesized via catalytic hydrogenation of double bond of enone derivatives.

Example 35

3-[({6-[5-(3-Benzo[b]furan-5-ylpropanoyl)-4-hydroxy-2-methoxyphenyl]-1-deoxy-β-D-glucopyranos-1-yl}carbonyl]propionic acid (Compound 47)

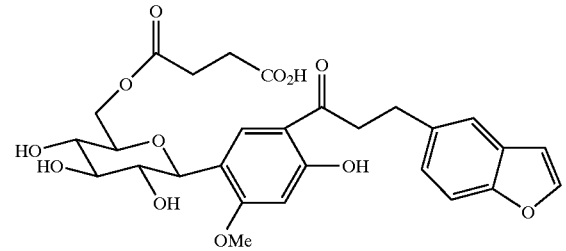

To a solution of the compound 22 (330 mg) in pyridine (5 mL) was added succinic anhydride (144 mg), the reaction mixture was stirred at room tempareture for 12 hr. The reaction mixture was poured into ice-water, and extracted with ethyl acetate. Organic layer was washed with brine, dried over $Na_2SO_4$, and concentrated. The crude product was purified by silicagel column chromatography (20:1 chloroform/MeOH) to give the desired compound (0.14 g) in 34.8% yield. mp=113–114° C., $[\alpha]^{23}_D$=–18.39 (C=0.5, MeOH)
Mass (m/e,ESI): 557(M–H)$^-$
$^1$H-NMR ($CDCl_3$)δ: 2.67(m,4H),2.96(t,2H,J=7.8 Hz), 3.10–5.07(m,12H),3.83(s,3H),6.42(s,1H),6.72(s,1H), 6.96–7.73(m,5H),12.87(s,1H)

Example 36

3-(Benzo[b]furan-5-yl)-3'-(6-sulfonic acid-β-D-glucopyranosyl)-4'-methoxy-6'-hydroxyacrylophenone (Compound 44)

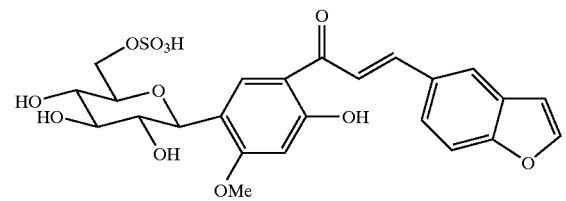

To a solution of the compound 3 (60 mg) in DMF (2 mL) was added DMF $SO_3$ complex (403 mg), and then stirred at room temperature for 2 hr. To the reaction mixture was added EtOH-AcOEt (4:1), and stirred whereupon the desired product (38 mg) precipitated as red crystals in 54% yield. mp-177–179° C.
Mass(m/e,ESI): 537(M+H)$^+$
IR ($cm^{-1}$)3382,1637,1563,1467,1368,1257,1107,1086,993
$^1$H-NMR (DMSO+$CD_3$OD) δ: 3.36(m,1H),3.46(m,2H),3.65 (dd,1H,J=5.7 Hz), 3.67–3.83(m,2H),3.95(s,3H),6.63(s, 1H),7.07(d,1H,J=2.0 Hz),7.73(d,1H, J=8.8 Hz),7.97(dd, 1H,J=8.8 Hz,2.0 Hz),8.01–8.10(m,3H),8.23(d,2H,J=10.7 Hz)

Example 37

3-(Benzo[b]furan-5-yl)-3'-(6-carboxysodium salt-β-D-glucopyranosyl)4'-methoxy-6'-hydroxy-acrylophenone (Compound 43)

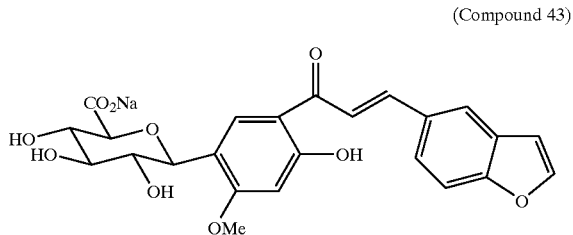

To a solution of the compound 3 (100 mg) in acetonitrile (3 mL) was TEMPO (4 mg) and KBr (4 mg) at room temperature, and then added satd. $NaHCO_3$ aq. (3 mL) and NaOCl (3 mL). The reaction mixture was stirred for 30 min, and diluted AcOEt (50 mL), neutralized with 10% HCl. Organic layer was dried over $Na_2SO_4$, and concentrated. The residue was purified by silicagel column chromatography (1:10 $MeOH/CHCl_3$) to give carboxylic acid (63 mg) in 61% yield. To a solution of this carboxylic acid (63 mg) in acetone (1 mL) was added 1 equiv. of NaOH (5 mg), and stirred for 30 min, evaporated to give 43 mg of desired compound. mp=115–117° C.
Mass(m/e,ESI): 492(M+H)+
IR ($cm^{-1}$)3364,1608,1548,1446,1257,1152,108,735,594
$^1$H-NMR ($D_2O$) δ: 3.30(m,1H),3.54(m,3H),3.83(s,3H),4.55(m,1H),6.27(s, 1H),6.95(s,1H)7.60–8.10(m,7H)

Example 38

4-({2-(3-Benzo[b]furan-5-ylpropanoyl)-5-methoxy-4-(β-D-glucopyranosyl) phenoxy} methyl)-5-methy-1,3-dioxolene-2-one (Compound 49)

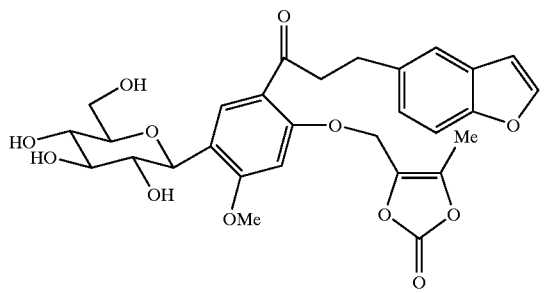

To a solution of the compound 22 (0.25 g) in DMF (3 mL) was added potassium carbonate (75 mg) and 4-bromomethyl-5-methyl-1,3-dioxolen-2-one (0.13 g), the reaction mixture was stirred at room temperature for 3 hr. The reaction mixture was poured into ice-water and extracted with ethyl acetate. Organic layer was washed with brine, dried over $Na_2SO_4$, and concentrated. The crude product was purified by silicagel column chromatography (20:1 chloroform/MeOH) to give 42 mg of the desired compound.
mp=128–128.5° C., [α]$^{23}_D$=+2.80 (C=1.0, MeOH)
Mass(m/e,ESI): 539(M+Na)+
$^1$H-NMR ($CDCl_3$) δ: 2.05(s,3H),2.90(t,2H,J=7.8 Hz), 3.07–3.89(m,9H),3.91 (s, 3H),4.54–4.69(ABq,2H),6.47 (s,1H),6.73(s,1H),6.80–7.10(ABq,2H),7.39(s, 1H),7.59 (s,1H),7.85(s,1H)

Example 39

According to a similar procedure described in Example 35, the compound 46 was obtained from the compound 3, using 4 equiv. of succinic anhydride.

Example 40

According to a similar procedure described in Example 35, the compound 42 was synthesized from the compound 3 as a starting materials.

Example 41–43

According to a similar procedure described in Example 37, the compound 45, 48 and 50 were synthesized from the corresponding carboxylic acid.

Example 44

3-(Benzo[b]furan-5-yl)-1-[6-hydroxy-4-methyl-2-{(β-D-glucopyranos-1-yl)methyl}]propiophenone (Compound 52)

(a) 1-[6-Hydroxy-4-methyl-2-{(2,3,4,6-tetra-O-benzyl-β-D-glucopyranosyl) methyl}]acetophenone (Compound 59)

Instead of 1,3-dimethoxy-5-iodebenzene,2-bromo-6-hydroxy-4-methyl acetophenone was reacted in a similar manner described in Example 1 to obtain the compound 59 in 53% yield.
Mass (m/e,ESI): 709(M+Na)+,687(M+H)+
IR ($cm^{-1}$): 2914,1359,1083,750,696
$^1$H-NMR ($CDCl_3$) δ: 2.21(s,3H),2.59(s,3H),2.97–3.01(m, 1H),3.22–3.67(m,8H), 4.42–5.00(m,8H),6.68(s,1H),6.67 (s,1H),7.18–7.38(m,20H),11.7(s,1H)

(b) 3-(Benzo[b]furan-5-yl)-1-[6-hydroxy-methyl-2-{(2,3,4,6-tetra-O-benzyl)-β-D-glucopyranosyl methyl}]acrylophenone (Compound 60)

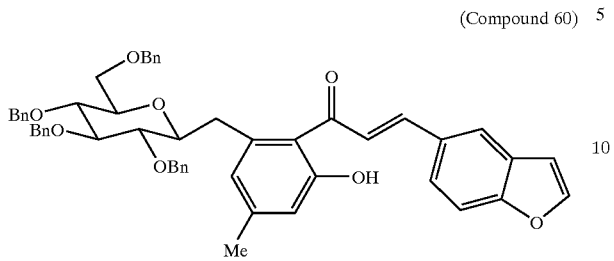

To a mixture of 9.89 g of the compound obtained from the above mentioned step (a) and 2.31 g of 5-benzofuranaldehyde in EtOH (140 mg), was added 50% KOH (17 mL) at 0° C. The mixture was stirred at room tempareture for 40 hr. To this mixture was added water and extracted with ethyl acetate. Organic layer was washed with brine, dried over $Na_2SO_4$, and evaporated. The crude product was purified by silicagel column chromatography (10:1 n-hexane/AcOEt) to give the compound 60 (7.2 g) in 61% yield.

Mass (m/e,ESI): 837(M+Na)$^+$,815(M+H)$^+$,849(M+Cl),813 (M−H)$^−$
IR (cm$^{-1}$): 1732,1628,1578,1240,1100,760
$^1$H-NMR (CDCl$_3$) δ: 2.27(s,3H),3.07–3.80(m,9H), 4.40–4.94(m,8H),6.70(s,1H), 6.73(s,1H),6.76(dd,1H,J=1.0 Hz,2.0 Hz),7.14–7.81(m,26H),10.8(s,1H)

(c) 3-(Benzo[b]furan-5-yl)-1-[6-hydroxy-4-methyl-2-{(β-D-glucopyranos-1-yl)methyl}]acrylophenone (Compound 51)

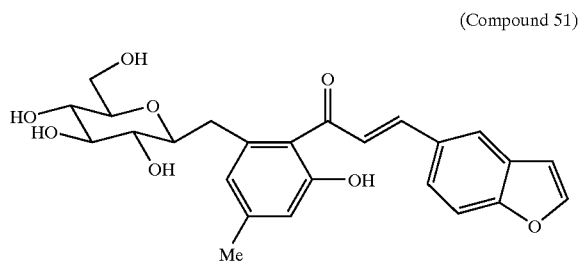

To a mixture of 7.2 g of the compound obtained from the above mentioned step (b) in $CH_2Cl_2$ (86 mL), was added BBr$_3$ (1.0M $CH_2Cl_2$ solution, 53 mL) at −78° C. The mixture was stirred for 2 hr at −78° C.→room temperature. The reaction mixture was poured into ice-water (200 mL) and extracted with ethyl acetate. Organic layer was washed with water, satd. NaHCO$_3$ and brine, dried over $Na_2SO_4$, and concentrated. The crude product was purified by silicagel column chromatography (20:1 chloroform/MeOH) to give the compound 51 (3.0 g) in 76% yield.

Mass (m/e,ESI): 455(M+H)$^+$,453(M−H)$^−$
IR (cm$^{-1}$): 3394,3004,2908,1575,1443,1263,1215,1089
$^1$H-NMR (CDCl$_3$) δ: 2.27(s,3H),2.89–3.75(m,13H),6.68(d, 2H,J=12.7 Hz) 6.77(d,1H,J=1.5 Hz),7.08(d,1H,J=16.1 Hz),7.47–7.53(m,2H),7.63–7.66(m, 2H),7.77(s,1H),8.68 (bs,1H)

(d) 3-(Benzo[b]furan-5-yl)-1-[6-hydroxy-4-methyl-2-1{(β-D-glucopyranos-1-yl)methyl}]propiophenone (Compound 52)

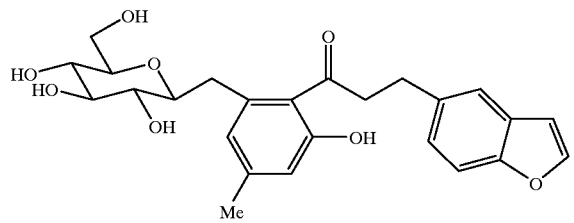

To a mixture of 3.0 g of the compound obtained from the above mentioned step (c) in MeOH (100 mL), were added DMAP (0.81 g) and 5% Pt-C (0.30 g). After stirring under hydrogen at room temperature for 20 hr. The mixture was filtered and evaporated. The residue was purified by silicagel column chromatography (10:1 chloroform/MeOH) to give the compound 52 (2.5 g) in 83% yield.
Mass (m/e,ESI): 456(M$^+$),438,305,261,175,131(BP),91
IR (cm$^{-1}$): 3394,2908,1614,1083,1032
$^1$H-NMR (CDCl$_3$) δ: 2.24(s,3H),2.47–3.73(m,15H),6.62(d, 1H,J=2.2 Hz),6.68(s, 1H),7.08(d,1H,J=8.8 Hz),7.37–7.57 (m,2H),7.57(s,1H),8.83(bs,1H)

Example 45

3-Benzo [b]furan-5-yl-1-(6-hydroxy-4-methyl-2-{[6-methoxycarbonyl-β-D-glucopyranos-1-yl]methyl})propiophenone (Compound 53)

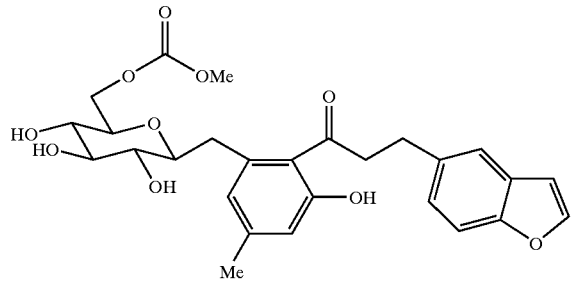

According to a similar procedure described in Example 4, 5 and 6, the compound 53 was synthesized from the compound 52 which obtained as described above Example 44.

Example 46

1-[2,4-Dihydroxy-6-{(β-D-glicopyranosyl)methyl}phenyl]-3-(4-hydroxyphenyl)propan-1-one
(Compound 54)

(Compound 54)

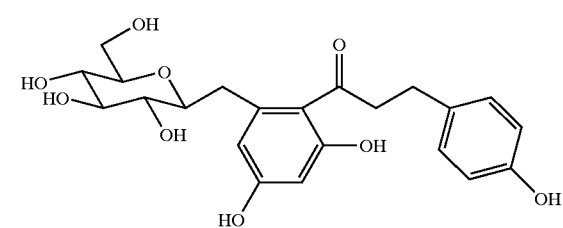

Instead of 1-[6-hydroxy-4-methyl-2-{(2,3,4,6-tetra-O-benzyl-β-D-glucopyranosyl)methyl}]acetophenone (Compound 59) and 5-benzofuranaldehyde,1-[2,4-dihydroxy-6-{(2,3,4,6-tetra-O-benzyl-β-D-glucopyranosyl)methyl}]acetophenone and 4-benzyloxybenzaldehyde were reacted in a similar manner described in Example 44 step (b), to obtained enone derivatives (1.2 g). To a mixture of this compound in methanol (20 mL), was added 1.2 g of 5% Pd-C. After stirring under hydrogen at room temperature for 6 hr, the reaction mixture was filtered and evaporated. The residue was purified by silicagel column chromatography (4:1 chloroform/MeOH) to give the compound 54 (0.52 g) in 88% yield. mp=227–228° C., $[\alpha]^{23}_D$=−10.80 (C=1.0, MeOH)

Mass (m/e,ESI): 457(M+Na)$^+$,469(M+Cl)$^-$,433(M−H)$^-$

IR (cm$^{-1}$): 3358,2914,1605,1510,1460,1365,1260,1160, 1100,840

$^1$H-NMR (DMSO:CDCl$_3$=2:1) δ: 2.43(dABq,1H,J=15.1 Hz),2.75(t,2H,J=7.6 Hz), 2.87–3.64(m,10H),4.56(t,1H,J= 5.9 Hz),4.77(d,1H,J=4.9 Hz),4.81(d,1H, J=4.4 Hz),4.91 (d,1H,J=5.4 Hz),6.61(d,1H,J=2.0 Hz),6.20(d,1H,J=2.0 Hz), 6.64(d,1H,J=8.8 Hz),7.00(d,2H,J=8.3 Hz),8.99(s, 1H),9.32(s,1H),9.59(s,1H)

Reference 4

1-[2,4-Dihydroxy-6-{(β-D-glucopyranosyl)methyl}] acetophenone (Compound 61)

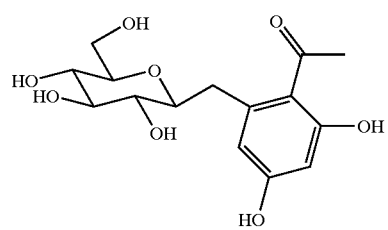

According to similar procedure described in Example 44 step (c), the compound 61 was obtained from 1.5 g of 1-[2,4-dihydroxy-6-[(2,3,4,6-tetra-O-benzyl-β-D-glucopyranosyl)methyl}]acetophenone in 57% yield (0.41 g). This compound was also used as a materials when synthesized the compound 54. mp=227–228° C., $[\alpha]^{23}_D$=−12.00 (C=1.0, MeOH)

Mass (m/e,ESI): 351(M+Na)$^+$,329(M+H)$^+$

IR (cm$^{-1}$): 3394,1599,1455,1353,1269,1161,1083,1008, 843,573

$^1$H-NMR (CDCl$_3$) δ: 2.47(s,3H),2.59(dABq,1H,J=14.7 Hz), 2.91–3.50(m,7H), 3.65(dABq,1H,J=11.7 Hz),4.25(bs, 5H),6.18(d,1H,J=2.0 Hz),6.27(d,1H, J=2.4 Hz),9.88(bs, 1H)

Example 47 and 48

According to a similar procedure described in Example 44, the compound 55 and 56 were synthesized via aldol reaction and catalytic hydrogenation of double bond of enone derivatives, respectively.

Example 49

Instead of 5-benzofuranaldehyde,5-benzothiophenealdehyde was reacted in a similar manner described in Example 44 step (b) followed by step (c), to obtain the compound 57.

Example 50

According to a similar procedure described in Example 4, 5, and 6, the compound 58 was synthesized via three steps that involve protection of phenolic hydroxy groups, reaction of primary hydroxy group, and removal of allyl group.

Effect of the Invention

A novel C-glycoside of this invention show Na$^+$-glucose cotransporter inhibition activity, and it is stable to hydrolysis by β-glucosidase and under the condition of acids and bases, and also useful for the agent of therapy/prophylaxis of diabetics and hypoglycemic agent.

What is claimed is:

1. A compound of the general formula (I),

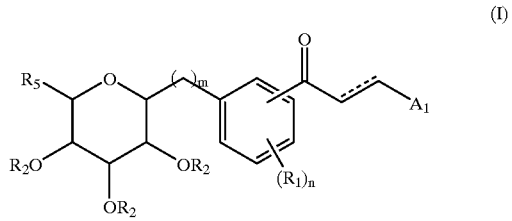

(I)

wherein

R$_1$ is H, OH, C$_{1-5}$ alkyl, O—C$_{1-5}$ alkyl or

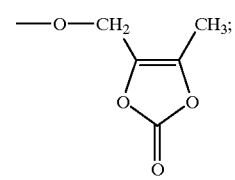

R$_2$ is H, —COO—C$_{1-5}$ alkyl,

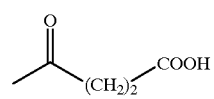

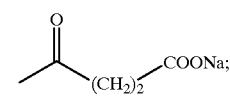

R$_5$ is —CH$_2$OH, —CH$_2$OCO$_2$—C$_{1-5}$ alkyl,

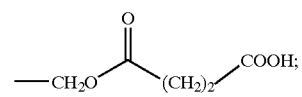

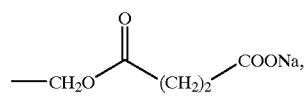

—CH$_2$OSO$_3$H, —COOH or COONa;

wherein $A_1$ is

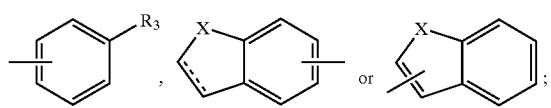

X is oxygen, nitrogen, sulfur;
═══ is optionally a saturated or unsaturated bond; and
m is 0 or 1;
n is 0, 1 or 2; wherein
  when m is 0, $R_3$ is $C_{1-5}$ alkyl; and
  when m is 1, $R_3$ is $C_{1-5}$ alkyl, —OH, or —O—$C_{1-5}$ alkyl;
or a pharmaceutically acceptable salt.

2. A process of the production of a compound of the general formula (I) as claimed in claim 1, comprising the steps of:
reacting a compound of the General formula (II)

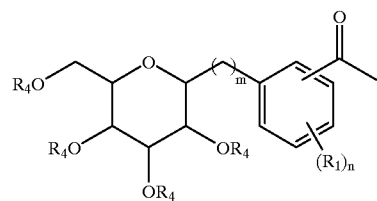 (II)

wherein
  $R_4$ is H, acetyl or benzyl group,
  $R_1$ is H, OH, $C_{1-5}$ alkyl, O—$C_{1-5}$ alkyl or,

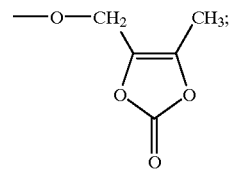

m is 0 or 1;
n is 0, 1 or 2; wherein
  when m is 0, $R_3$ is $C_{1-5}$ alkyl; and
  when m is 1, $R_3$ is $C_{1-5}$ alkyl, —OH, or —O—$C_{1-5}$ alkyl;
with general formula (IV)

$$OHC—A_1 \qquad (IV)$$

wherein $A_1$ is

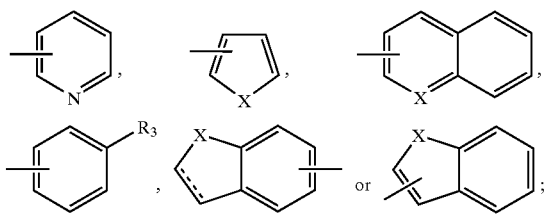

X is oxygen, nitrogen, sulfur;
═══ is optionally a saturated or unsaturated bond; and
m is 0 or 1;
n is 0, 1 or 2; wherein
  when m is 0, $R_3$ is $C_{1-5}$ alkyl; and
  when m is 1, $R_3$ is $C_{1-5}$ alkyl, —OH, or —O—$C_{1-5}$ alkyl
by aldol condensation and following reduction, if desired.

3. A blood glucose lowering agent comprising a compound represented by general formula (I) of claim 1 or its pharmaceutically acceptable salt in admixture with a pharmaceutically acceptable carrier.

* * * * *